US00RE37585E

(19) United States
(12) Reissued Patent
Mourou et al.

(10) Patent Number: US RE37,585 E
(45) Date of Reissued Patent: Mar. 19, 2002

(54) METHOD FOR CONTROLLING CONFIGURATION OF LASER INDUCED BREAKDOWN AND ABLATION

(75) Inventors: Gérard Mourou, Ann Arbor, MI (US); Detao Du, Fremont, CA (US); Subrata K. Dutta, Ann Arbor, MI (US); Victor Elner, Ann Arbor, MI (US); Ron Kurtz, Ann Arbor, MI (US); Paul R. Lichter, Ann Arbor, MI (US); Xinbing Liu, Acton, MA (US); Peter P. Pronko, Dexter, MI (US); Jeffrey A. Squier, San Diego, CA (US)

(73) Assignee: The Regents of the University of Michigan, Ann Arbor, MI (US)

(21) Appl. No.: 09/366,685

(22) Filed: Aug. 4, 1999

Related U.S. Patent Documents

Reissue of:
(64) Patent No.: 5,656,186
Issued: Aug. 12, 1997
Appl. No.: 08/224,961
Filed: Apr. 8, 1994

(51) Int. Cl.[7] ..... B23K 26/02; B23K 26/40
(52) U.S. Cl. ..... 219/121.69
(58) Field of Search ..... 219/121.6, 121.61, 219/121.62, 121.67, 121.68, 121.69, 121.7, 121.71, 121.72, 121.73, 121.75, 121.78, 121.79, 121.8, 121.81, 121.83; 216/65; 606/10, 11, 12; 372/25, 24; 378/122

(56) References Cited

U.S. PATENT DOCUMENTS 3,720,213 A * 3/1973 Hobart et al.
4,001,840 A * 1/1977 Becker et al.
4,087,672 A * 5/1978 Yi ..... 219/121.68
4,114,018 A * 9/1978 Von Allmen et al. ... 219/121.69
4,289,378 A * 9/1981 Remy et al.
4,464,761 A * 8/1984 Alfano et al.
4,579,430 A * 4/1986 Bille
4,630,274 A * 12/1986 Schäfer
4,665,913 A * 5/1987 L'Esperance, Jr.
4,675,500 A * 6/1987 Kunz et al. ..... 219/121.73
4,712,543 A * 12/1987 Baron (List continued on next page.)

FOREIGN PATENT DOCUMENTS

DE 41 19024 A1 * 12/1992
JP 62-93095 * 4/1987
WO 89/08529 * 3/1989

OTHER PUBLICATIONS

C.V. Shank, R. Yen and C. Hirlimann, "Time Resolved Reflectivity Measures of Femtosecond–Optical–Pulse–Induced Phase transitions in Silicon", Physical Review Letters, vol. 50, No. 6, 454–457, Feb. 7, 1983.*

(List continued on next page.)

*Primary Examiner*—Geoffrey S. Evans
(74) *Attorney, Agent, or Firm*—Young & Basile, P.C.

(57) ABSTRACT

In one aspect the invention provides a method for laser induced breakdown of a material with a pulsed laser beam where the material is characterized by a relationship of fluence breakdown threshold ($F_{th}$) versus laser beam pulse width (T) that exhibits an abrupt, rapid, and distinct change or at least a clearly detectable and distinct change in slope at a predetermined laser pulse width value. The method comprises generating a beam of laser pulses in which each pulse has a pulse width equal to or less than the predetermined laser pulse width value. The beam is focused to a point at or beneath the surface of a material where laser induced breakdown is desired.

The beam may be used in combination with a mask in the beam path. The beam or mask may be moved in the x, y, and Z directions to produce desired features. The technique can produce features smaller than the spot size and Rayleigh range due to enhanced damage threshold accuracy in the short pulse regime.

53 Claims, 10 Drawing Sheets

U.S. PATENT DOCUMENTS

| | | | | | |
|---|---|---|---|---|---|
| 4,727,381 | A | * | 2/1988 | Bille et al. | |
| 4,729,372 | A | * | 3/1988 | L'Esperance, Jr. | |
| 4,732,473 | A | * | 3/1988 | Bille et al. | |
| 4,733,660 | A | * | 3/1988 | Itzkan | |
| 4,764,930 | A | * | 8/1988 | Bille et al. | |
| 4,838,679 | A | * | 6/1989 | Bille | |
| 4,839,493 | A | * | 6/1989 | Herziger et al. | 219/121.69 |
| 4,848,340 | A | * | 7/1989 | Bille et al. | |
| 4,881,808 | A | * | 11/1989 | Bille et al. | |
| 4,901,718 | A | * | 2/1990 | Bille et al. | |
| 4,907,586 | A | * | 3/1990 | Bille et al. | |
| 4,925,523 | A | * | 5/1990 | Braren et al. | |
| 4,930,505 | A | * | 6/1990 | Hatje | |
| 4,942,586 | A | * | 7/1990 | Lai | |
| 4,988,348 | A | * | 1/1991 | Bille | |
| 5,062,702 | A | * | 11/1991 | Bille | |
| 5,093,548 | A | * | 3/1992 | Schmidt-Hebbel | 219/121.71 |
| 5,098,426 | A | * | 3/1992 | Sklar et al. | |
| 5,141,506 | A | * | 8/1992 | York | |
| 5,207,668 | A | * | 5/1993 | L'Esperance, Jr. | |
| 5,208,437 | A | * | 5/1993 | Miyauchi et al. | 219/121.83 |
| 5,219,343 | A | * | 6/1993 | L'Esperance, Jr. | |
| 5,235,606 | A | * | 8/1993 | Mourou et al. | 372/25 |
| 5,246,435 | A | * | 9/1993 | Bille et al. | |
| 5,269,778 | A | * | 12/1993 | Rink et al. | 606/12 |
| 5,280,491 | A | * | 1/1994 | Lai | 372/24 |
| 5,289,407 | A | * | 2/1994 | Strickler et al. | |
| 5,312,396 | A | * | 5/1994 | Feld et al. | |
| 5,335,258 | A | * | 8/1994 | Whitlock | 378/122 |
| 5,348,018 | A | * | 9/1994 | Alfano et al. | 606/10 |
| 5,389,786 | A | * | 2/1995 | Itoh et al. | 250/307 |
| 5,454,902 | A | * | 10/1995 | Zinck et al. | 219/121.69 |
| 5,558,789 | A | * | 9/1996 | Singh | 219/121.69 |
| 5,984,916 | A | * | 11/1999 | Lai | 606/11 |

OTHER PUBLICATIONS

C.V. Shank, R. Yen, and C. Hirlimann, "Femtosecond–Time Resolved Surface Structural Dynamics of Optically Excited Silicon", Physical Review Letters, vol. 51, No. 10, 900–902, Sep. 5, 1983.*

C.V. Shank and M.C. Downer, "Femtosecond Dynamics of Highly Excited Semiconductors", Mat. Res. Soc. Symp. Proc., vol. 51, 15–23, 1985.*

S. Küper and M. Stuke, "Femtosecond uv Excimer Laser Ablation", Applied Physics B, vol. 44, 199–201, Jun. 7, 1993.*

S. Preuss, M. Späth, Y. Zhang, and M. Stuke, "Time Resolved Dynamics of Subpicosecond Laser Ablation", Applied Physics Letters, vol. 62, No. 23, 3049–3051, Jun. 7, 1993.*

A.M. Malvezzi, N. Bloembergen, and C.Y. Huang, "Time–Resolved Picosecond Optical Measurements of Laser–Excited Graphite", Physical Review Letters, vol. 57, No. 1, 146–149, Jul. 7, 1986.*

D.H. Reitzke, X. Wang, H. Ahn, and M.C. Downer, "Femtosecond Laser Melting of Graphite", Physical Review B, vol. 40, No. 17, Dec. 15, 1989.*

F. Muller, K. Mann, R. Simon, J.S. Bernstein, and G.J. Zaal, "A comparative Study of Decomposition of Thin Films by Laser Induced PVD with Femtosecond and Nanosecond Laser Pulses", SPIE vol. 1858, pp. 464–475, 1993.*

International Search Report Form PCT/ISO/210 Dated Jul. 31, 1995 and Mailed Aug. 4, 1995.*

M.W. Berns et al., "Laser Microsurgery in Cell and Developmental Biology", Science, vol. 213, No. 31, pp. 505–513, Jul. 1981.*

G.L. LeCarpentier et al. "Continuous Wave Laser Ablation of Tissue: Analysis of Thermal and Mechanical Events", IEEE Transactions on Biomedical Engineering, vol. 40, No. 2, 188–200, Feb. 1993.*

C. LeBlanc, "Realization and Characterization of a High Intensity Femtosecond Laser System Based on all Titanium Doped Sapphire", Annales de Physique, vol. 19, No. 1, Abstract, Feb. 1994.*

R. Birngruber, C. Puliafito, A. Gawande, W. Lin, R. Schoenlein, and J. Fujimoto, "Femtosecond Laser–Tissue Interactions: Retinal Injury Studies", IEEE Journal of Quantum Electronics, vol. QE–23, No. 10, 1836–1844, Oct. 1987.*

B. Zysset, J. Fujimoto, and T. Deutsch, "Time–Resolved Measurements of Picosecond Optical Breakdown", Applied Physics B48, 139–147 (1989).*

B. Zysset, J. Fujimoto, C. Puliafito, R. Bingruber, and T. Deutsch, "Picosecond Optical Breakdown: Tissue Effects and Reduction of Collateral Damage", Lasers in Surgery and Medicine 9:192–204 (1989).*

S. Watanabe, R. Anderson, S. Brorson, G. Dalickas, J. Fujimoto, and T. Flotte, "Comparative Studies of Femtosecond to Microsecond Laser Pulses on Selective Pigmented Cell Injury in Skin", Photochemistry and Photobiology vol. 53, No. 6, 757–762, 1991.*

N. Bloembergen, "Laser–Induced Electric Breakdown in Solids", IEEE Journal of Quantum ELectronics, vol. QE–10, No. 3, (Mar. 1974).*

R. Birngruber, C. Puliafito, A. Gawande, W. Lin, R. Schoenlein, and J. Fujimoto, Femtosecond Laser–Tissue Interactions: Retinal Injury Studies, IEEE Log. No. 8716039, (1987).*

D. Stern, R. Schoenlein, C. Puliafito, E. Dobi, R. Birngruber and J. Fujimoto, "Corneal Ablation by Nanosecond, Picosecond, and Femtosecond Lasers at 532 and 625 nm", Arch Opthalmol, vol. 107, (Apr. 1989).*

J. Squier, F. Salin, and G. Mourou, "100–fs Pulse Generation and Amplification in $TiAl_2O_3$", Optics letters, vol. 16, No. 5 (Mar. 1991).*

B. Frueh, J. Bille, and S. Brown, "Intrastromal Relaxing Excisions in Rabbits with a Picosecond Infrared Laser", Lasers and Light in Opthamology, vol. 4, No. 3/4, pp. 165–168, (1992).*

R. Remmel, C. Dardenne, and J. Bille, "Intrasomal Tissue Removed Using an Infrared Picosecond Nd:YLF Opthalmic Laser Operating at 1053 nm", Lasers and Light in Opthamology, vol. 4, No. 3/4, 169–173, (1992).*

J. Squier and G. Mourou, "Tunable Solid State Lasers Create Ultrashort Pulses", Laser Focus World, (Jun. 1992).*

M.H. Niemz, T.P. Hoppeler, T. Juhasz, and J. Bille, "Intrastromal Ablations for Refractive Corneal Surgery Using Picosecond Infrared Laser Pulses", Lasers and Light in Opthamology, vol. 5, No. 3, pp. 149–155, 1993.*

H. Cooper, J. Schuman, C. Puliafito, D. McCarthy, W. Woods, N. Friedmann, N. Wang, and C. Lin, "Picosecond Neodymium:Yttrium Lithium Fluoride Laser Sclerectomy", Am. Journal of Opth. 115:221–224, (Feb. 1993).*

K. Frederickson, W. White, R. Wheeland, and D. Slaughter, "Precise Ablation of Skin with Reduced Collateral Damage Using the Femtosecond–Pulsed, Terawatt Titanium–Sapphire Laser", Arch Dermatol, vol. 129, (Aug. 1993).*

H. Kapteyn and M. Murnane, "Femtosecond Lasers: The next Generation", Optics & Photonics News, (Mar. 1994).*

G. Mourou, A. Zewail, P. Barbara, and W. Knox, "New Generation of Ultrafast Sources Marked by Higher Powers, Versatility" Optics & Photonics News (Mar. 1994).*

D. Du, X. Lin, G. Korn, J. Squier, and G. Morou, "Laser-Induced Breakdown by Impact Ionization in $SiO_2$ with Pulse Widths from 7 ns to 150 fs", Appl. Phys. letters 64 (23), (Jun. 6, 1994).*

* cited by examiner $I \sim e^{-(x/\sigma)^2}$ $I = I_o e^{\frac{-2R^2}{W^2}}$ $f_1$, $f_2$ - FOCAL LENGTH OF LENSES
$f_1 = mf_2$ WHERE m IS ARBITRARY

IMAGING SYSTEM

MASK - CROSS HATCHED AREAS
ARE OPAQUE TO LASER WAVELENGTH

TARGET BEING
ABLATED WITH MASK

TARGET AFTER ABLATION IS ESSENTIALLY
IMAGE OF MASK.

DAMAGE ALONG THE Z AXIS

METHOD FOR CONTROLLING CONFIGURATION OF LASER INDUCED BREAKDOWN AND ABLATION

Matter enclosed in heavy brackets [ ] appears in the original patent but forms no part of this reissue specification; matter printed in italics indicates the additions made by reissue.

GOVERNMENT RIGHTS

This invention was made with government support provided by the Office of Naval Research and the National Science Foundation under the terms of No. STC PHY 8920108. The government has certain rights in the invention.

*Notice: More than one reissue application has been filed for the reissue of U.S. Pat. No. 5,656,186. The reissue applications are application numbers 09/366,685 (the present application), which has divisional applications 09/775,069 and 09/775,106.*

FIELD OF THE INVENTION

This invention relates generally to methods utilizing lasers for modifying internal and external surfaces of material such as by ablation or changing properties in structure of materials. This invention may be used for a variety of materials.

BACKGROUND OF THE INVENTION

Laser induced breakdown of a material causes chemical and physical changes, chemical and physical breakdown, disintegration, ablation, and vaporization. Lasers provide good control for procedures which require precision such as inscribing a micro pattern. Pulsed rather than continuous beams are more effective for many procedures, including medical procedures. A pulsed laser beam comprises bursts or pulses of light which are of very short duration, for example, on the order of 10 nanoseconds in duration or less. Typically, these pulses are separated by periods of quiescence. The peak power of each pulse is relatively high often on the order of gigawatts and capable of intensity on the order of $10^{13}$ w/cm$^2$. Although the laser beam is focused onto an area having a selected diameter, the effect of the beam extends beyond the focused area or spot to adversely affect peripheral areas adjacent to the spot. Sometimes the peripheral area affected is several times greater than the spot itself. This presents a problem, particularly where tissue is affected in a medical procedure. In the field of laser machining, current lasers using nanosecond pulses cannot produce features with a high degree of precision and control, particularly when nonabsorptive wavelengths are used.

It is a general object to provide a method to localize laser induced breakdown. Another object is to provide a method to induce breakdown in a preselected pattern in a material or on a material.

SUMMARY OF THE INVENTION

In one aspect the invention provides a method for laser induced breakdown of a material with a pulsed laser beam where the material is characterized by a relationship of fluence breakdown threshold ($F_{th}$) versus laser beam pulse width (T) that exhibits an abrupt, rapid, and distinct change or at least a clearly detectable and distinct change in slope at a predetermined laser pulse width value. The method comprises generating a beam of laser pulses in which each pulse has a pulse width equal to or less than the predetermined laser pulse width value. The beam is focused to a point at or beneath the surface of a material where laser induced breakdown is desired.

In one aspect, the invention may be understood by further defining the predetermined laser pulse width as follows: the relationship between fluence breakdown threshold and laser pulse defines a curve having a first portion spanning a range of relatively long (high) pulse width where fluence breakdown threshold ($F_{th}$) varies with the square root of pulse width ($T^{1/2}$). The curve has a second portion spanning a range of short (low) pulse width relative to the first portion. The proportionality between fluence breakdown threshold and pulse width differ in the first and second portions of the curve and the predetermined pulse width is that point along the curve between its first and second portions. In other words, the predetermined pulse width is the point where the $F_{th}$ versus $\tau_p$ relationship no longer applies, and, of course, it does not apply for pulse widths shorter than the predetermined pulse width.

The scaling of fluence breakdown threshold ($F_{th}$) as a function of pulse width (T) is expressed as $F_{th}$ proportional to the square root of ($T^{1/2}$) is demonstrated in the pulse width regime to the nanosecond range. The invention provides methods for operating in pulse widths to the picosecond and femtosecond regime where we have found that the breakdown threshold (Fth) does not vary with the square root of pulse width ($T^{1/2}$).

Pulse width duration from nanosecond down to the femtosecond range is accomplished by generating a short optical pulse having a predetermined duration from an optical oscillator. Next the short optical pulse is stretched in time by a factor of between about 500 and 10,000 to produce a timed stretched optical pulse to be amplified. Then, the time stretched optical pulse is amplified in a solid state amplifying media. This includes combining the time stretched optical pulse with an optical pulse generated by a second laser used to pump the solid state amplifying media. The amplified pulse is then recompressed back to its original pulse duration.

In one embodiment, a laser oscillator generates a very short pulse on the order of 10 to 100 femtoseconds at a relatively low energy, on the order of 0.001 to 10 nanojoules. Then, it is stretched to approximately 100 picoseconds to 1 nanosecond and 0.001 to 10 nanojoules. Then, it is amplified to typically on the order of 0.001 to 1.000 millijoules and 100 picoseconds to 1 nanosecond and then recompressed. In its final state it is 10 to 200 femtoseconds and 0.001 to 1.000 millijoules. Although the system for generating the pulse may vary, it is preferred that the laser medium be sapphire which includes a titanium impurity responsible for the lasing action.

In one aspect, the method of the invention provides a laser beam which defines a spot that has a lateral gaussian profile characterized in that fluence at or near the center of the beam spot is greater than the threshold fluence whereby the laser induced breakdown is ablation of an area within the spot. The maximum intensity is at the very center of the beam waist. The beam waist is the point in the beam where wave-front becomes a perfect plane; that is, its radius of curvature is infinite. This center is at radius R=0 in the x-y axis and along the Z axis, Z=0. This makes it possible to damage material in a very small volume Z=0, R=0. Thus it is possible to make features smaller than spot size in the x-y focal plane and smaller than the Rayleigh range (depth of focus) in the Z axis. It is preferred that the pulse width duration be in the femtosecond range although pulse duration of higher value may be used so long as the value is less than the pulse width defined by an abrupt or discernable change in slope of fluence breakdown threshold versus laser beam pulse width.

In another aspect, a diaphragm, disk, or mask is placed in the path of the beam to block at least a portion of the beam to cause the beam to assume a desired geometric configuration. In still further aspects, desired beam configurations are achieved by varying beam spot size or through Fourier Transform (FT) pulse shaping to cause a special frequency distribution to provide a geometric shape.

It is preferred that the beam have an energy in the range of 10 nJ (nanojoules) to 1 millijoule and that the beam have a fluence in the range of 0.1 $J/cm^2$ to 100 $J/cm^2$ (joules per centimeter square). It is preferred that the wavelength be in a range of 200 nm (nanometer) to 1 $\mu$m (micron).

Advantageously, the invention provides a new method for determining the optimum pulse width duration regime for a specific material and a procedure for using such regime to produce a precisely configured cut or void in or on a material. For a given material the regime is reproducible by the method of the invention. Advantageously, very high intensity results from the method with a modest amount of energy and the spot size can be very small. Damage to adjoining area is minimized which is particularly important to human and animal tissue.

These and other object features and advantages of the invention will be become apparent from the following description of the preferred embodiments, claims, and accompanying drawings.

DETAILED DESCRIPTION OF THE PREFERRED EMBODIMENTS

Figure 1:
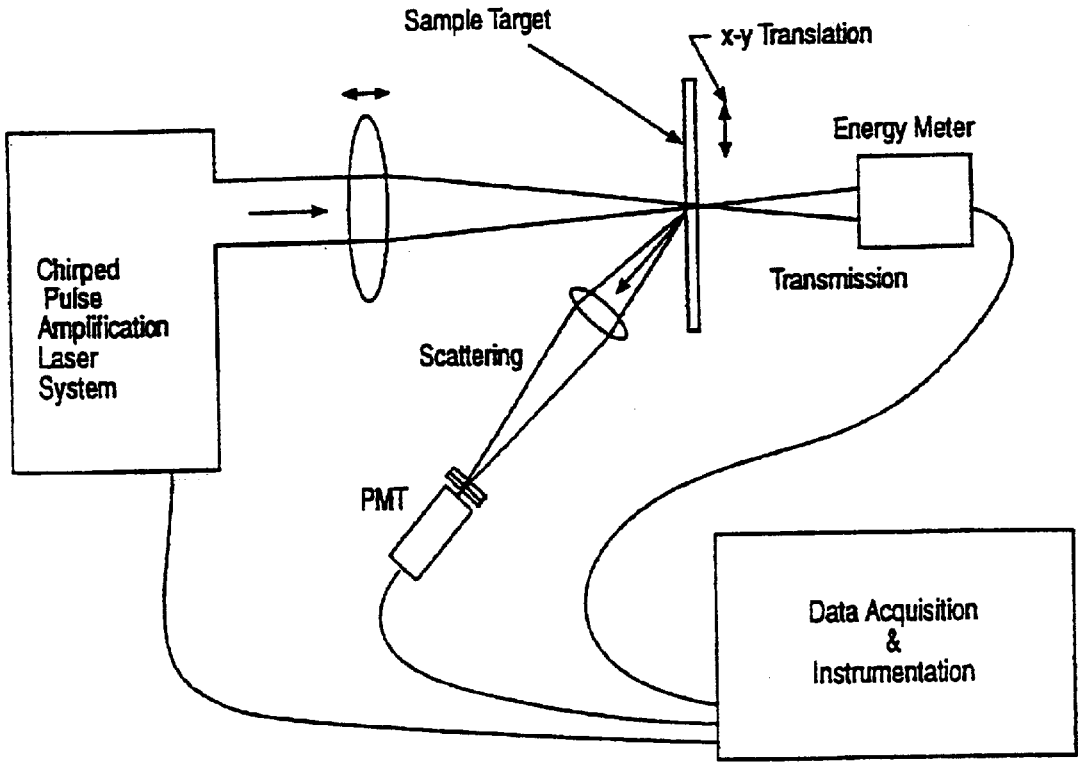
FIG. 1 is a schematic representation of a laser induced breakdown experimental system which includes a chirped pulse amplification laser system and means for detecting scattered and transmitted energy. If the sample is transparent, then transmitted energy can also be measured.

Referring to FIG. 1 there is shown an apparatus for performing tests to determine the laser induced breakdown threshold as a function of laser pulse width in the nanosecond to femtosecond range using a chirped-pulse amplification (CPA) laser system. The basic configuration of such a CPA system is described in U.S. Pat. No. 5,235,606 which is assigned to the assignee of the present invention and which has inventors in common with this present application. U.S. Pat. No. 5,235,606 is incorporated herein by reference in its entirety.

Chirped-pulse amplification systems have been described by Jeffrey Squier and Gerard Mourou, two of the joint inventors in the present application, in a publication entitled Laser Focus World published by Pennwell in June of 1992. It is described that CPA systems can be roughly divided into four categories. The first includes the high energy low repetition systems such as ND glass lasers with outputs of several joules but they may fire less than 1 shot per minute. A second category are lasers that have an output of approximately 1 joule and repetition rates from 1 to 20 hertz. The third group consists of millijoule level lasers that operate at rates ranging from 1 to 10 kilohertz. A fourth group of lasers operates at 250 to 350 kilohertz and produces a 1 to 2 microjoules per pulse. In U.S. Pat. No. 5,235,606 several solid state amplifying materials are identified and the invention of U.S. Pat. No. 5,235,606 is illustrated using the Alexandrite. The examples below use Ti:Sapphire and generally follow the basic process of U.S. Pat. No. 5,235,606 with some variations as described below.

The illustrative examples described below generally pertain to pulse energies less than a microjoule and often in the nanojoule range with pulse duration in the range of hundreds of picoseconds or less and the frequency on the order of 1 kilohertz. But these examples are merely illustrative and the invention is not limited thereby.

In a basic scheme for CPA, first a short pulse is generated. Ideally the pulse from the oscillator is sufficiently short so that further pulse compression is not necessary. After the pulse is produced it is stretched by a grating pair arranged to provide positive group velocity dispersion. The amount the pulse is stretched depends on the amount of amplification. Below a millijoule, tens of picoseconds are usually sufficient. A first stage of amplification typically takes place in either a regenerative or a multipass amplifier. In one configuration this consists of an optical resonator that contains the gain media, a Pockels cell, and a thin film polarizer. After the regenerative amplification stage the pulse can either be recompressed or further amplified. The compressor consists of a grating or grating pair arranged to provide negative group velocity dispersion. Gratings are used in the compressor to correspond to those in the stretching stage. More particulars of a typical system are described in U.S. Pat. No. 5,235,606, previously incorporated herein by reference.

An important aspect of the invention is the development of a characteristic curve of fluence breakdown threshold $F_{th}$ as a function of laser pulse width specific to a material. Then identify on such curve, the point at which there is an abrupt, or distinct and rapid change or at least a discernable change in slope characteristic of the material. In general it is more desirable to operate past this point because of the more precise control of the laser induced breakdown (LIB) or ablation threshold.

EXAMPLE 1

Opaque Material

FIG. 1 shows an experimental setup for determining threshold fluence by determining scattered energy versus incident fluence and by determining threshold fluence versus pulse width. The system includes means for generating a pulsed laser beam as described earlier, and means, typically a lens, for collecting emission from the target to a photomultiplier tube. Change of transmission through a transparent sample is measured with an energy meter.

Figure 2:
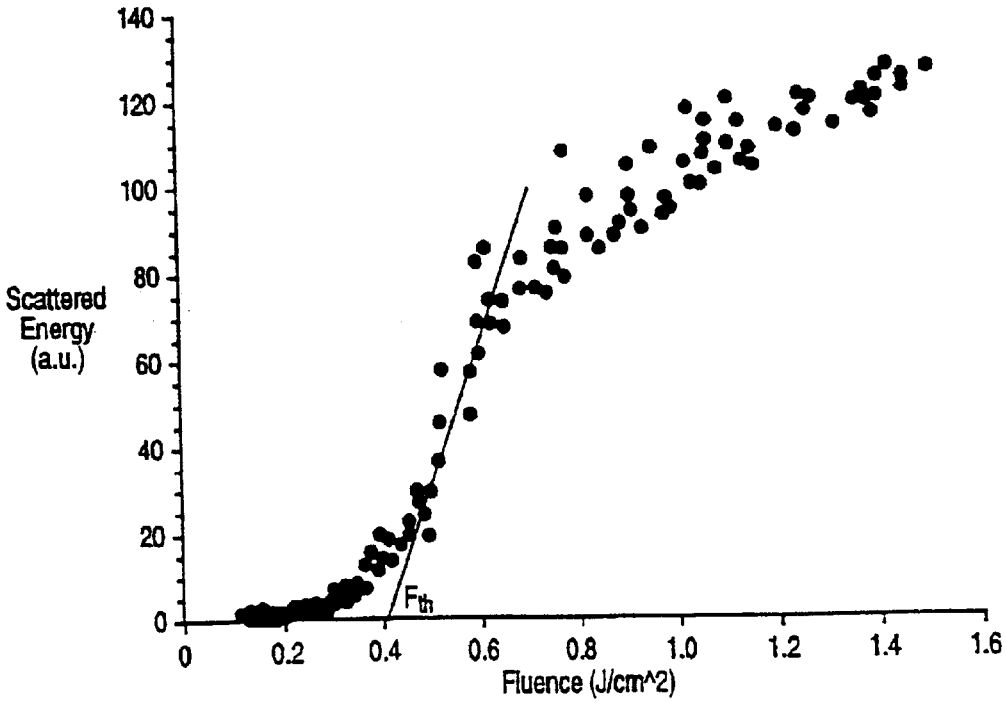
FIG. 2 is a plot of scattered energy versus incident fluence obtained for an opaque (gold) sample using the system in FIG. 1 operated for 150 femtoseconds (fs) pulse duration.
Figure 3:
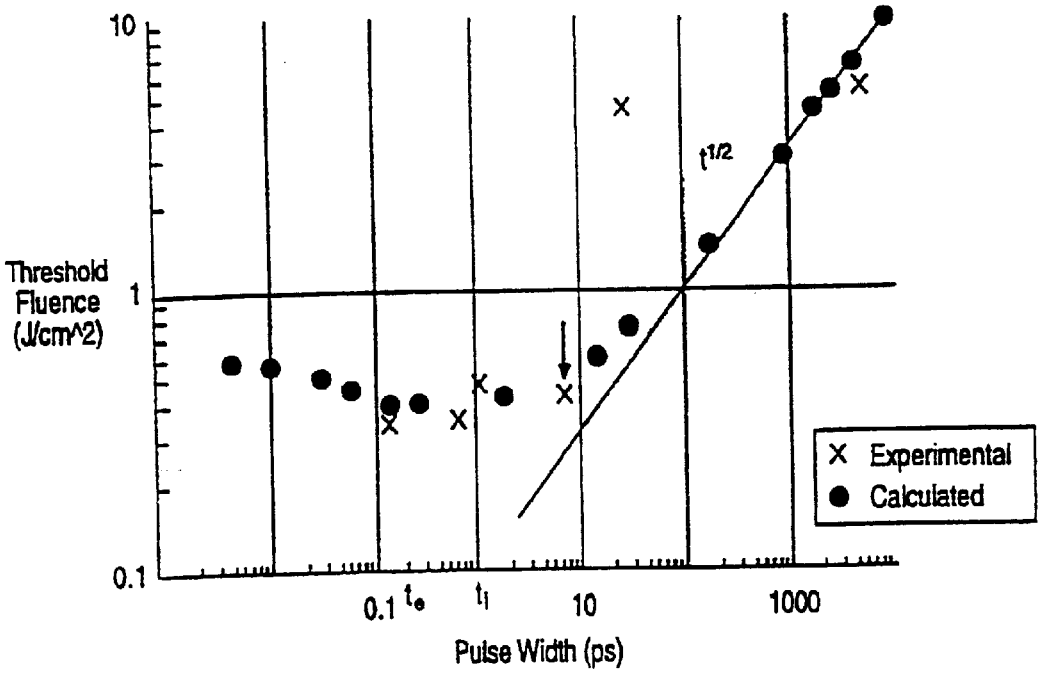
FIG. 3 is a plot of calculated and experimental values of threshold fluence versus pulse width for gold, with experimental values obtained for the gold sample using the system of FIG. 1 operated at 800 nm wavelength. The arrow shows the point on the plot where the $F_{th}$ proportional to $T^{1/2}$ no longer applies, as this relationship only holds for pulse widths down to a certain level as shown by the solid line.

FIG. 2 shows a plot of data obtained from an absorbing medium which is gold using 150 fs pulse and FIG. 3 shows threshold fluence versus pulse width. The arrow in FIG. 3 identifies the point at which the relationship between the threshold fluence and pulse width varies dramatically.

Figure 4:
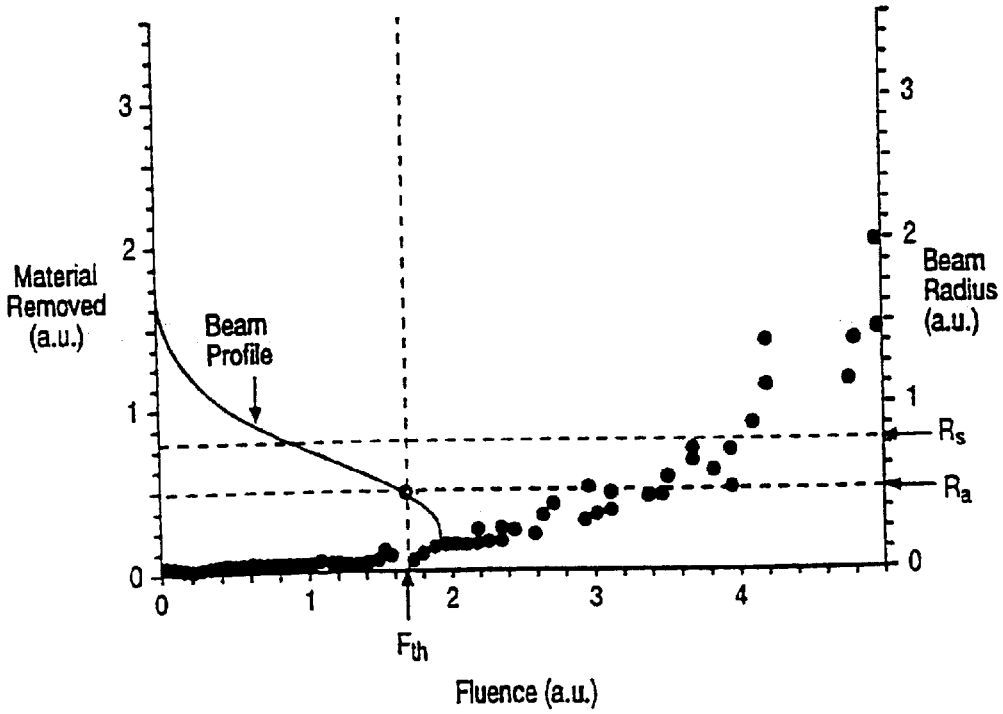
FIG. 4 is a graphical representation of sub-spot size ablation/machining in gold based on arbitrary units and showing $F_{th}$ the threshold fluence needed to initiate material removal; Rs the spot size of the incident beam and Ra the radius of the ablated hole in the x-y plane.
Figure 5:
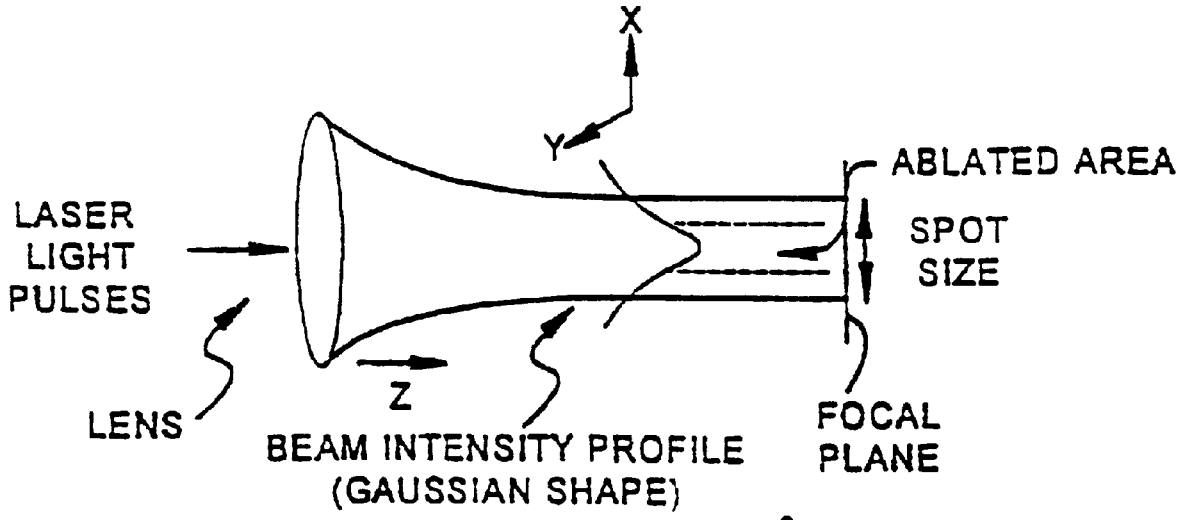
FIG. 5 is a schematic illustration of a beam intensity profile showing that for laser micro-machining with ultrafast pulse according to the invention, only the peak of the beam intensity profile exceeds the threshold intensity for ablation/machining.

In experimental conditions with wavelength of 800 nm and 200 fs pulses on gold (FIG. 3), the absorption depth is 275 A with a diffusion length of 50 A. In the case of nanosecond pulses the diffusion length, which is on the order of 10 $\mu$m (micron) in diameter, is much longer than the absorption depth, resulting in thermal diffusion being the limiting factor in feature size resolution. Empirical evidence for the existence of these two regimes is as exhibited in FIG. 3. Here both experimental and theoretical ablation thresholds are plotted as a function of pulse width. An arrow at approximately 7 picoseconds pulse width (designated herein as T or $\tau_p$) delineates the point (or region closely bounding that point) at which the thermal diffusion length ($L_{th}$) is equal to the absorption depth (1/a). It is clear that for a smaller size spot a shorter (smaller) pulse is necessary. For spot size on the order of 1000 Å or less, pulse width on the order of 100 femtoseconds or less will be needed. It is clear from the figure that this is the point at which the ablation threshold transitions from a slowly varying or nearly constant value as a function of pulse width to one that is dramatically dependent on pulse time. This result is surprising. It has been demonstrated that the electron thermalization time for laser deposited energy in gold is on the order of, or less than, 500 fs and the electron-lattice interaction time is 1 ps. The consequences of this four ultrafast laser pulses is that the energy is contained within the beam spot. In fact for energies at or near the threshold for ablation, the spatial profile of the laser beam will determine the size and shape of the region being ablated (FIGS. 4 and 5).

Additional experiments were performed to measure the amount of recombination light produced as a function of the fluence impinging on a gold film. The technique involved is based upon the experimental setup previously described. A basic assumption is that the intensity of the light is proportional to the amount of material ablated. In FIG. 4, the material removed is plotted as a function of fluence. A well defined threshold fluence is observed at which material removal is initiated. By having only a small fraction of the gaussian beam where the fluence is greater than the threshold, the ablated region can be restricted to this small area. In FIG. 4, $R_a$ is the radial position on the beam where the fluence is at threshold. Ablation, then, occurs only within a radius $R_a$. It is evident that by properly choosing the incident fluence, the ablated spot or hole can in principle be smaller than the spot size, $R_s$. This concept is shown schematically in FIG. 5. Although the data for a 150 fs pulse is shown in FIG. 4, this threshold behavior is exhibited in a wide range of pulse widths. However, sub spot size ablation is not possible in the longer pulse regimes, due to the dominance of thermal diffusion as will be described below.

Additional experiments on opaque materials used a 800 nm Ti:Sapphire oscillator whose pulses were stretched by a grating pair, amplified in a regenerative amplifier operating at 1 kHz, and finally recompressed by another grating pair. Pulse widths from 7 ns to 100 fs were obtained. The beam was focused with a 10× objective, implying a theoretical spot size of 3.0 $\mu$m in diameter. A SEM photo-micrograph of ablated holes obtained in a silver film on glass, using a pulse width of 200 fs and a pulse energy of 30 nJ (fluence of 0.4 J/cm$^2$) produced two holes of diameter approximately 0.3 $\mu$m in diameter. Similar results have been obtained in aluminum.

These results suggest that by, producing a smaller spot size which is a function of numerical aperture and wavelength, even smaller holes can be machined. We have demonstrated the ability to generate the fourth harmonic (200 nm) using a nonlinear crystal. Thus by using a stronger objective lens along with the 200 nm light, holes with diameters of 200 angstroms could in principle be formed.

These examples show that by using femtosecond pulses the spatial resolution of the ablation/machining process can be considerably less than the wavelength of the laser radiation used to produce it. The ablated holes have an area or diameter less than the area or diameter of the spot size. In the special case of diffraction limited spot size, the ablated hole has a size (diameter) less than the fundamental wavelength size. We have produced laser ablated holes with diameters less than the spot diameter and with diameters 10% or less of the laser beam spot size. For ultrafast pulses in metals the thermal diffusion length, $l_{th}=(Dt)^{1/2}$ (where D is the thermal diffusivity and t the pulse time), is significantly smaller than the absorption depth (1/a), where a is the absorption coefficient for the radiation.

Those skilled in the art will understand that the basic method of the invention may be utilized in alternative embodiments depending on the desired configurations of the induced breakdown. Examples include, but are not limited to using a mask in the beam path, varying spot size, adjusting focus position by moving the lens, adjusting laser cavity design, Fourier Transform (FT) shaping, using a laser operating mode other than TEMoo, and adjusting the Rayleigh range, the depth of focus or beam waist.

Figure 6A:
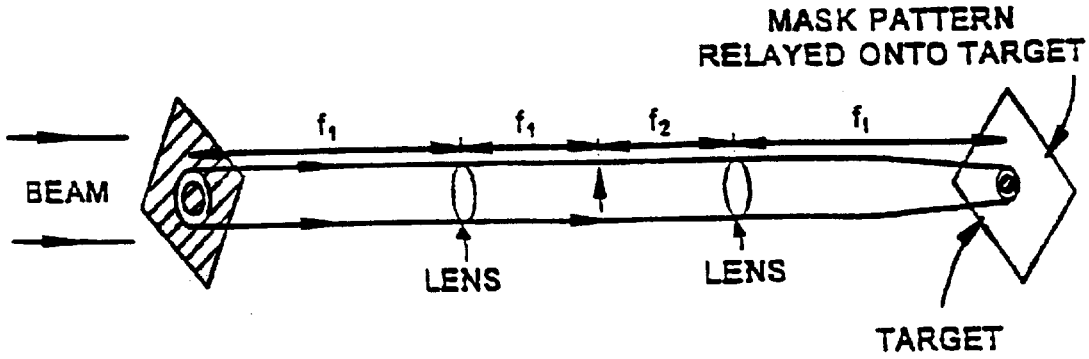
FIG. 6A and B are schematic illustrations of a beam showing the placement of a disk-shaped mask in the beam path.
Figure 6B:
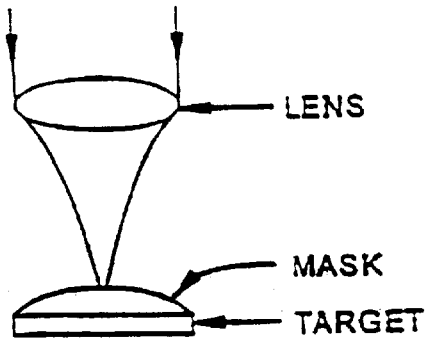
Figure 6B:
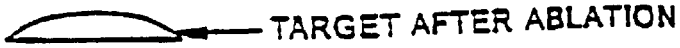

The use of a mask is illustrated in FIG. 6A and B. The basic method consists of placing a mask in the beam path or on the target itself. If it is desired to block a portion of the beam, the mask should be made of an opaque material and be suspended in the beam path (FIG. 6) alternatively, the mask may be placed on the target and be absorptive so as to contour the target to the shape of the mask (FIG. 6B).

The varying spot size is accomplished by varying the laster f/#, varying the focal length of the lens or input beam size to the lens as by adjustable diaphragm.

Operation in other than the TEMoo mode means that higher order transverse modes could be used. This affects the beam and material as follows: the beam need not be circular or gaussian in intensity. The material will be ablated corresponding to the beam shape.

The Rayleigh range (Z axis) may be adjusted by varying the beam diameter, where the focal plane is in the x-y axis.

EXAMPLE 2

Transparent Material

A series of tests were performed on an $SiO_2$ (glass) sample to determine the laser induced breakdown (LIB) threshold as a function of laser pulse width between 150 fs–7 ns, using a CPA laser system. The short pulse laser used was a 10 Hz Ti:Sapphire oscillator amplifier system based on the CPA technique. The laser pulse was focused by an f=25 cm lens inside the $SiO_2$ sample. The Rayleigh length of the focused beam is ~2 mm. The focused spot size was measured in-situ by a microscope objective lens. The measured spot size FWHM (full width at half max) was 26 $\mu$m in diameter in a gaussian mode. The fused silica samples were made from Corning 7940, with a thickness of 0.15 mm. They were optically polished on both sides with a scratch/dig of 20–10. Each sample was cleaned by methanol before the experiment. Thin samples were used in order to avoid the complications of self-focusing of the laser pulses in the bulk. The $SiO_2$ sample was mounted on a computer controlled motorized X-Y translation stage. Each location on the sample was illuminated by the laser only once.

Figure 7:
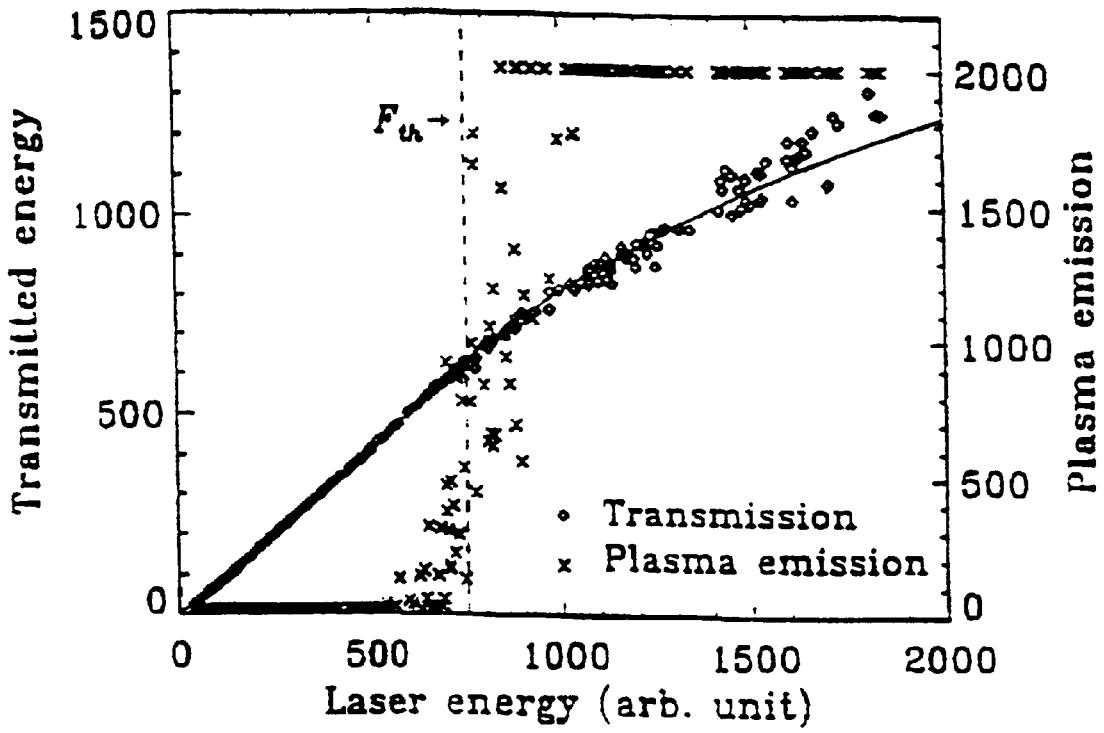
FIG. 7 is a plot of scattered plasma emission and transmitted laser pulse as a function of incident laser pulse energy for a transparent glass sample, $SiO_2$.

Two diagnostics were used to determine the breakdown threshold $F_{th}$. First, the plasma emission from the focal region was collected by a lens to a photomultiplier tube with appropriate filters. Second, the change of transmission through the sample was measured with an energy meter. (See FIG. 1) Visual inspection was performed to confirm the breakdown at a nanosecond pulse duration. FIG. 7 shows typical plasma emission and transmitted light signal versus incident laser energy plots, at a laser pulse width of $\tau_p$=300 fs. It is worth noting that the transmission changed slowly at around $F_{th}$. This can be explained by the temporal and spatial behavior of the breakdown with ultrashort pulses. Due to the spatial variation of the intensity, the breakdown will reach threshold at the center of the focus, and because of the short pulse duration, the generated plasma will stay localized. The decrease in transmitted light is due to the reflection, scattering, and absorption by the plasma. By assuming a gaussian profile in both time and space for the laser intensity, and further assuming that the avalanche takes the entire pulse duration to reach threshold, one can show that the transmitted laser energy $U_t$ as a function of the input energy U is given by $$U_t=kU,\ U\leq U_{th}$$

$$U_t=kU_{th}[1+\ln(U/U_{th})],\ U>U_{th}$$

where k is the linear transmission coefficient. The solid curve in FIG. 7 is plotted using Eq. (1) with $U_{th}$ as a fitting parameter. In contrast, breakdown caused by nanosecond laser pulses cuts off the transmitted beam near the peak of the pulses, indicating a different temporal and spatial behavior.

Figure 8:
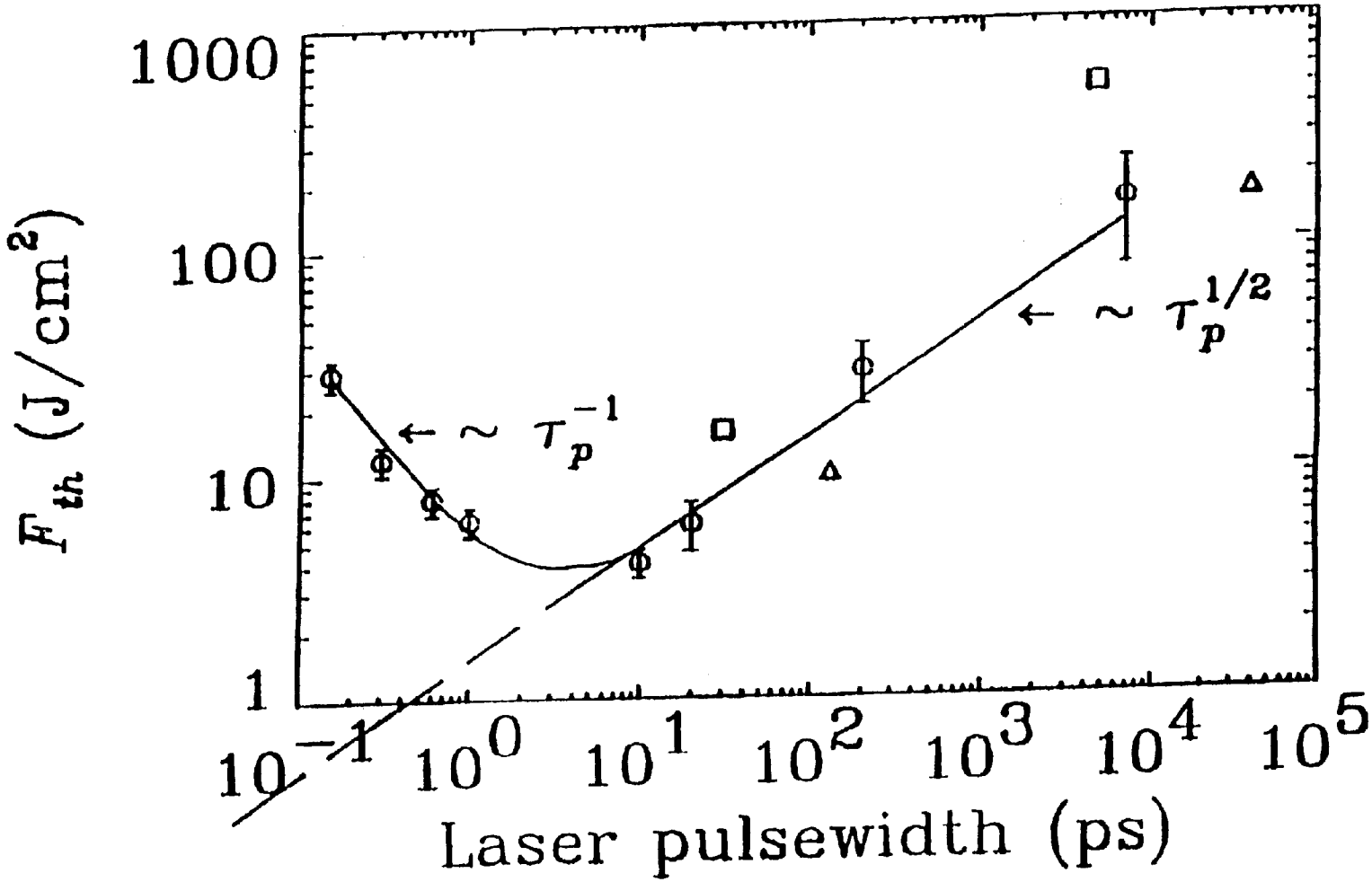
FIG. 8 is a plot of fluence threshold ($F_{th}$) versus pulse width (T) for the transparent glass sample of FIG. 7 showing that $F_{th}$ varying with $T^{1/2}$ only holds for pulse widths down to a certain level as shown by the solid line. Previous work of others is shown in the long pulse width regime (Squares, Smith Optical Eng 17, 1978 and Triangles. Stokowski, NBS Spec Bul 541, 1978).

FIG. 8 shows the fluence breakdown threshold $F_{th}$ as a function of laser pulse width. From 7 ns to about 10 ps, the breakdown threshold follows the scaling in the relatively long pulse width regime (triangles and squares) are also shown as a comparison—it can be seen that the present data is consistent with earlier work only in the higher pulse width portion of the curve. When the pulse width becomes shorter than a few picoseconds, the threshold starts to increase. As noted earlier with respect to opaque material (metal), this increased precision at shorter pulse widths is surprising. A large increase in damage threshold accuracy is observed, consistent with the multiphoton avalanche breakdown theory. (See FIGS. 8 and 9). It is possible to make features smaller than spot size in the x-y focal plane and smaller than the Rayleigh range (depth of focus) in the longitudinal direction or Z axis. These elements are essential to making features smaller than spot size or Rayleigh range.

EXAMPLE 3

Tissue

A series of experiments was performed to determine the breakdown threshold of cornea as a function of laser pulse width between 150 fs–7 ns, using a CPA laser system. As noted earlier, in this CPA laser system, laser pulse width can be varied while all other experimental parameters (spot size, wavelength, energy, etc.) remain unchanged. The laser was focused to a spot size (FWHM) of 26 $\mu$m in diameter. The plasma emission was recorded as a function of pulse energy in order to determine the tissue damage threshold. Histologic damage was also assessed.

Figure 9:
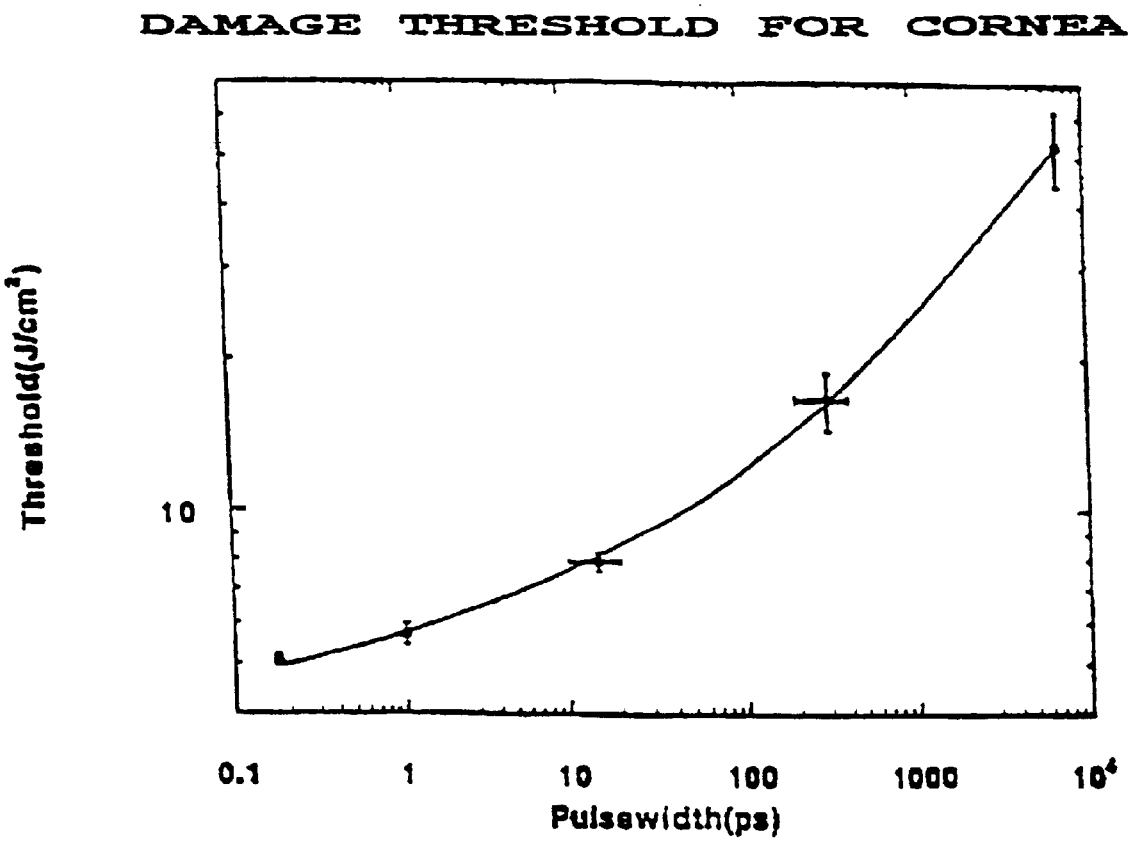
FIG. 9 is a plot of fluence threshold versus pulse width for corneal tissue, again showing that the proportionality between $F_{th}$ and pulse width follows the $T^{1/2}$ relationship only for pulse widths which are relatively long.
Figure 10:
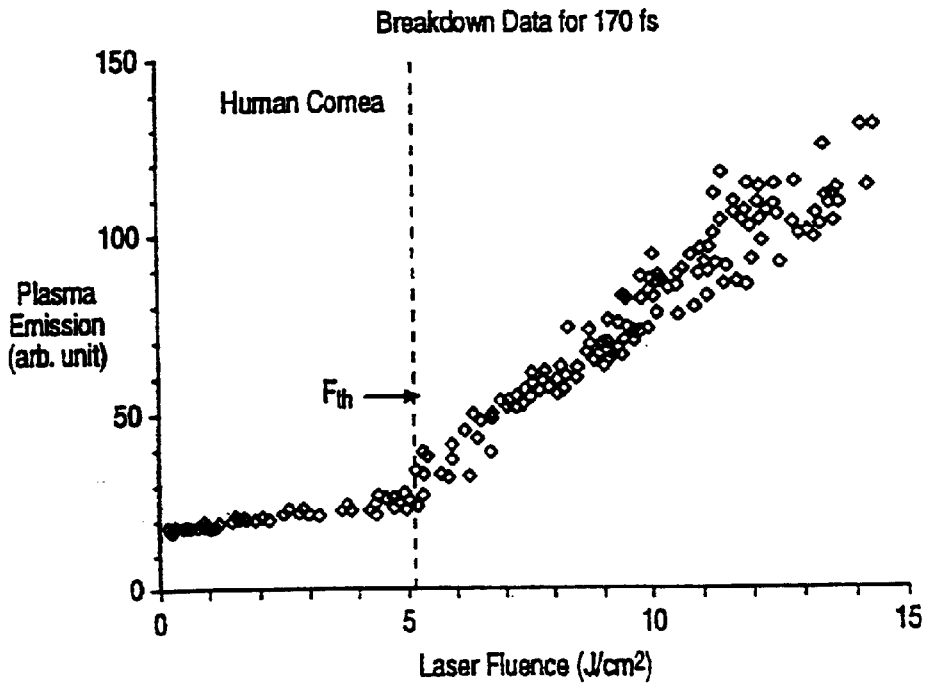
FIGS. 10 and 11 are plots of plasma emission versus laser fluence showing that at 170 (FIG. 10) pulse width the $F_{th}$ is very clearly defined compared to 7 nm (FIG. 11) pulse width where it is very unclear.
Figure 11:
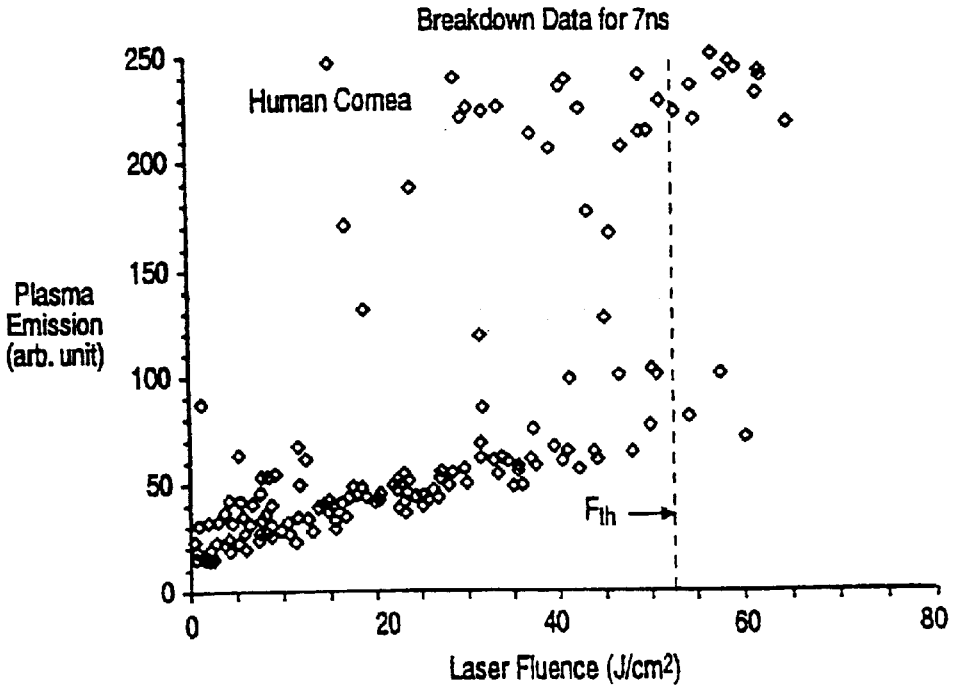

Breakdown thresholds calculated from plasma emission data revealed deviations from the scaling law. $F_{th} \propto T^{1/2}$, as in the case of metals and glass. As shown in FIG. 9, the scaling law of the fluence threshold is true to about 10 ps, and fail when the pulse shortens to less than a few picoseconds. As shown in FIGS. 10 and 11, the ablation or LIB threshold varies dramatically at high (long) pulse width. It is very precise at short pulse width. These results were obtained at 770 nm wavelength. The standard deviation of breakdown threshold measurements decreased markedly with shorter pulses. Analysis also revealed less adjacent histological damage with pulses less than 10 ps.

The breakdown threshold for ultrashort pulses (<10 ps) is less than longer pulses and has smaller standard deviations. Reduced adjacent histological damage to tissue results from the ultrashort laser pulses.

In summary, it has been demonstrated that subwavelength holes can be machined into metal surfaces using femtosecond laser pulses. The effect is physically understood in terms of the thermal diffusion length, over the time period of the pulse deposition, being less than the absorption depth of the incident radiation. The interpretation is further based on the hole diameter being determined by the lateral gaussian distribution of the pulse in relation to the threshold for vaporization and ablation.

Laser induced optical breakdown dielectrics consists of three general steps: free electron generation and multiplication, plasma heating and material deformation or breakdown. Avalanche ionization and multiphoton ionization are the two processes responsible for the breakdown. The laser induced breakdown threshold in dielectric material depends on the pulse width of the laser pulses. An empirical scaling law of the fluence breakdown threshold as a function of the pulse width is given by $F_{th} \propto \sqrt{\tau_p}$, or alternatively, the intensity breakdown threshold, $I_{th}=F_{th}/\tau_p$. Although this scaling law applies in the pulse width regime from nanosecond to tens of picoseconds, the invention takes advantage of the heretofore unknown regime where breakdown threshold does not follow the scaling law when suitably short laser pulses are used, such as shorter than 7 picoseconds for gold and 10 picoseconds for $SiO_2$.

While not wishing to be held to any particular theory, it is thought that the ionization process of a solid dielectric illuminated by an intense laser pulse can be described by the general equation $$dne(t)/dt=\eta(E)ne(t)+(dne(t)/dt)_{PI}-(dn_e(t)/dt)_{loss}$$

where $n_e(t)$ is the free electron (plasma) density, $\eta(E)$ is the avalanche coefficient, and E is the electric field strength. The second term on the right hand side is the photoionization contribution, and the third term is the loss due to electron diffusion, recombination, etc. When the pulse width is in the picosecond regime, the loss of the electron is negligible during the duration of the short pulse.

Photoionization contribution can be estimated by the tunneling rate. For short pulses, $E\sim10^8$ V/cm, the tunneling rate is estimated to be $w\sim4\times10^9$ $sec^{-1}$, which is small compared to that of avalanche, which is derived below. However, photoionization can provide the initial electrons needed for the avalanche processes at short pulse widths. For example, the data shows at 1 ps, the rms field threshold is about $5\times10^7$ V/cm. The field will reach a value of $3.5\times10^7$ V/cm (ms) at 0.5 ps before the peak of the pulse, and $w\sim100$ $sec^{-1}$. During a $\Delta t\sim100$ fs period the electron density can reach $n_e\sim n_t[1-\exp(-w\Delta t)]\sim10^{11}$ $cm^{-3}$, where $n_t\sim10^{22}$ is the total initial valence band electron density.

Neglecting the last two terms there is the case of an electron avalanche process, with impact ionization by primary electrons driven by the laser field. The electron density is then given by $n_e(t)=n_o\times\exp(n(E)t)$, where $n_o$ is the initial free electron density. These initial electrons may be generated through thermal ionization of shallow traps or photoionization. When assisted by photoionization at short pulse regime, the breakdown is more statistical. According to the condition that breakdown occurs when the electron density exceeds $n_{th}\cong10^{18}$ $cm^{-3}$ and an initial density of $n_o\cong19^{10}$ $cm^{-3}$, the breakdown condition is then given by $\eta\tau_p\cong18$. For the experiment, it is more appropriate to use $n_{th}\cong1.6\times10^{21}$ $cm^{-3}$, the plasma critical density, hence the threshold is reached when $\eta\tau_p\cong30$. There is some arbitrariness in the definition of plasma density relating to the breakdown threshold. However, the particular choice of plasma density does not change the dependence of threshold as function of pulse duration (the scaling law).

In the experiment, the applied electric field is on the order of a few tens of MV/cm and higher. Under such a high field, the electrons have an average energy of ~5 eV, and the electron collision time is less than 0.4 fs for electrons with energy $U\geqq5$–6 eV. Electrons will make more than one collision during one period of the electric oscillation. Hence the electric field is essentially a dc field to those high energy electrons. The breakdown field at optical frequencies has been shown to correspond to dc breakdown field by the relationship $E^{rmk}_{th}(w)=E^{dc}_{th}(1+w^2\tau^2)^{1/2}$, where w is the optical frequency and $\tau$ is the collision time.

In dc breakdown, the ionization rate per unit length, $\alpha$, is used to describe the avalanche process, with $\eta=\alpha(E)v_{drift}$, where $v_{drift}$ is the drift velocity of electrons. When the electric field is as high as a few MV/cm, the drift velocity of free electrons is saturated and independent of the laser electric field, $v_{drift}\cong2\times10^7$ cm/s.

The ionization rate per unit length of an electron is just $eE/U_i$ times the probability, P(E), that the electron has an energy $\geqq U_i$, or $\alpha(E)=(eE/U_i)P(E)$. Denoting $E_{kT,E}p$, and $E_i$ as threshold fields for electrons to overcome the decelerating effects of thermal, phonon, and ionization scattering, respectively. Then the electric field is negligible, $E<E_{kT}$, so the distribution is essentially thermal, P(E) is simply $\exp(-U_i/kT)$. It has been suggested: $P(E)\sim\exp(-const/E)$ for $E_{kT}<E<E_p$; $P(E)\sim\exp(-const/E^2)$ at higher fields ($E>E_p$). Combining the three cases the expression that satisfies both low and high field limits:

$$\alpha(E)=(eE/U_i)\exp(-Ei/(E(1+E/E_p)+E_{kT}).$$

This leads to $F_{th}\ \alpha\ E^2\tau_p\sim1/\tau_p$, i.e., the fluence threshold will increase for ultrashort laser pulses when $E>\sqrt{E_pE_i}$ is satisfied.

Figure 12:
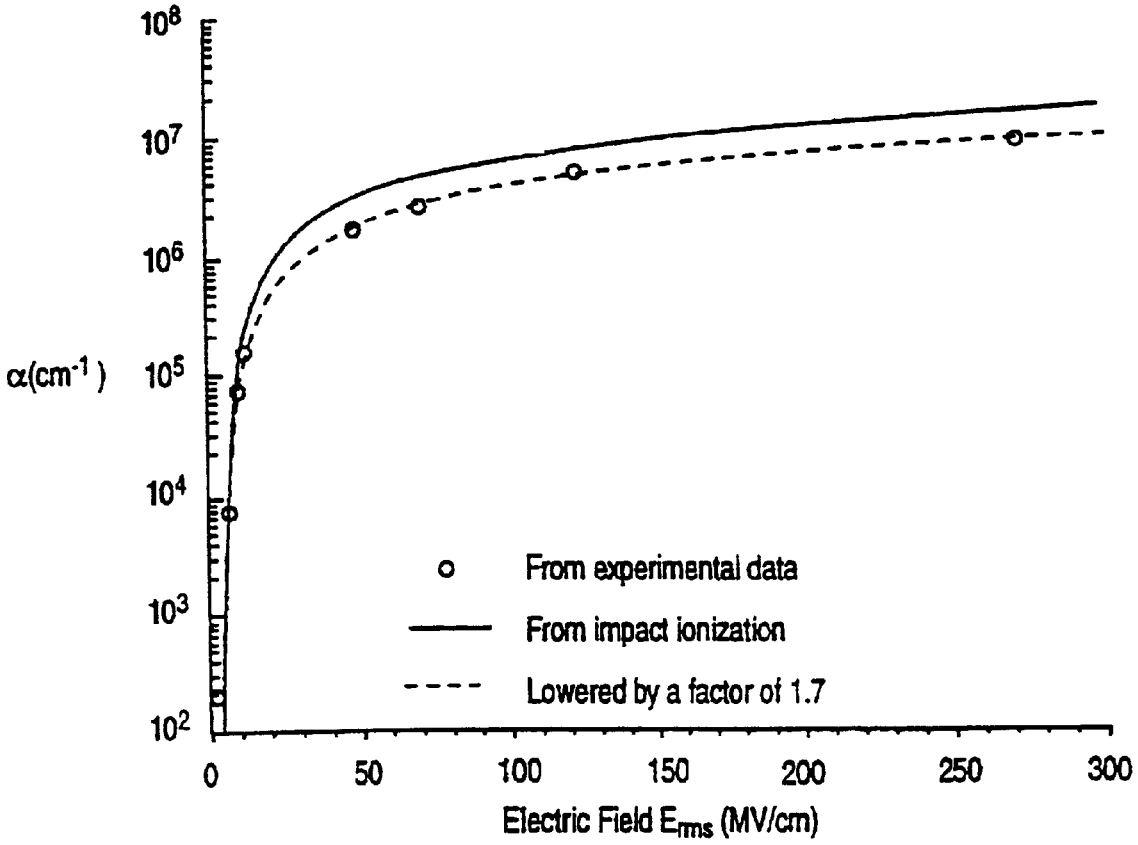
FIG. 12 is a plot of impact ionization rate per unit distance determined by experiment and theoretical calculation.

FIG. 12 is a plot of $\alpha$ as a function of the electric field, E. From experimental data, calculated according to $\eta\tau_p=30$ and $\eta=av_{drift}$. The solid curve is calculated from the above equation, using $E_i=30$ MV/cm, $E_p=3.2$ MV/cm, and $E_{kT}=0.01$ MV/cm. These parameters are calculated from U=eEl, where U is the appropriate thermal, phonon, and ionization energy, and l is the correspondent energy, relation length ($l_{kT}=l_p\sim5$ Å, the atomic spacing, and $l_i\cong30$ Å). It shows the same saturation as the experimented data. The dashed line is corrected by a factor of 1.7, which results in an excellent fit with the experimental data. This factor of 1.7 is of relatively minor importance, as it can be due to a systematic correction, or because breakdown occurred on the surface first, which could have a lower threshold. The uncertainty of the saturation value of $v_{drift}$ also can be a factor. The most important aspect is that the shape (slope) of the curve given by the equation provides excellent agreement with the experimental data. Thus, the mechanism of laser induced breakdown in fused silica (Example 2), using pulses as short as 150 fs and wavelength at 780 nm, is likely still dominated by the avalanche process.

Figure 13A:
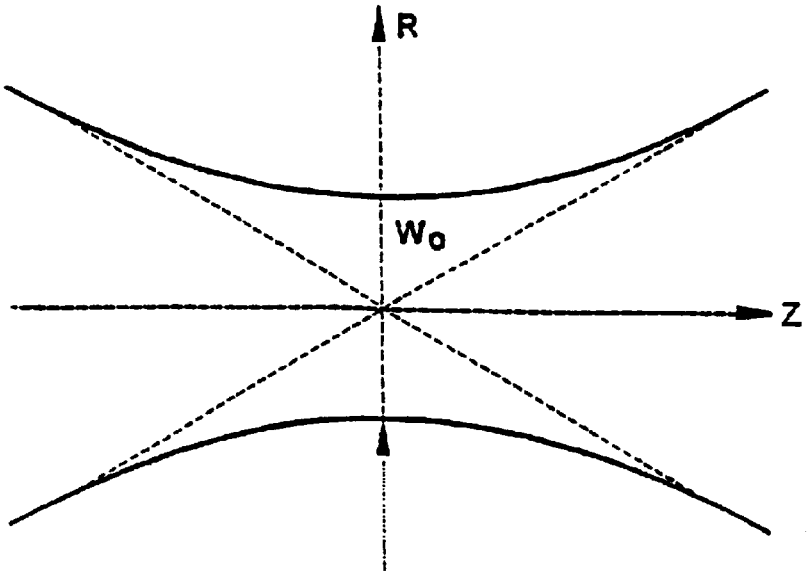
FIGS. 13A and B are schematic illustrations of beam profile along the longitudinal Z axis and sharing precise control of damage—dimension along the Z axis.
Figure 13B:
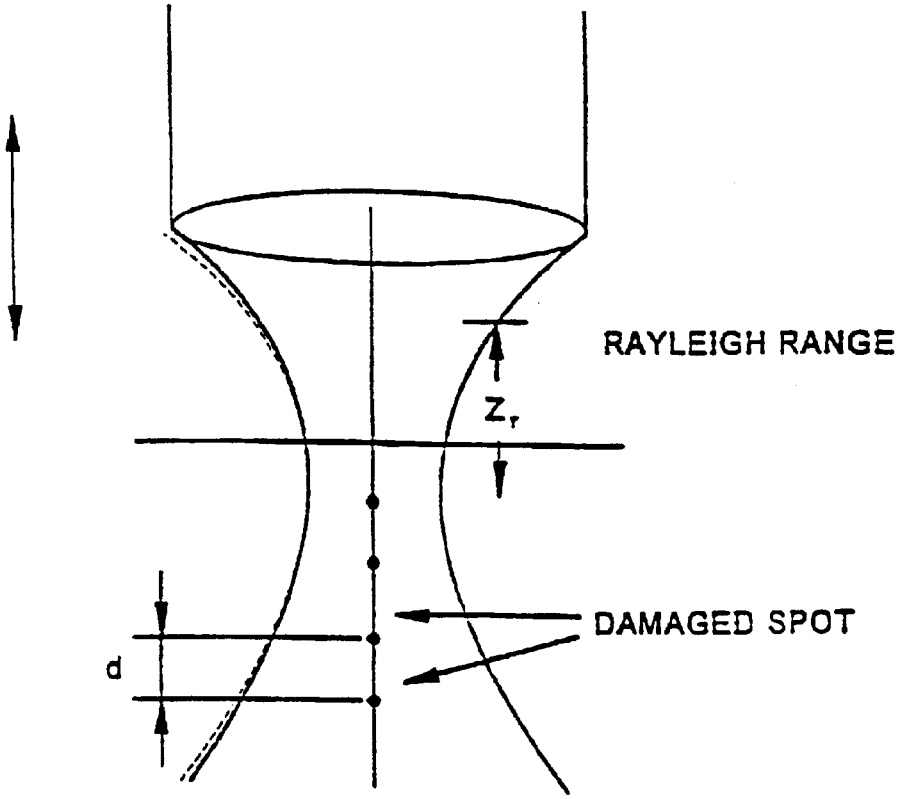

Opaque and transparent materials have common characteristics in the curves of FIGS. 3, 8, and 9 each begins with $F_{th}$ versus $T^{1/2}$ behavior but then distinct change from that behavior is evident. From the point of deviation, each curve is not necessarily the same since the materials differ. The physical characteristics of each material differ requiring a material specific analysis. In the case of $SiO_2$ (FIG. 8) the energy deposition mechanism is by dielectric breakdown. The optical radiation is releasing electrons by multiphoton ionization (M PI) that are tightly bound and then accelerating them to higher energies by high field of the laser. It is thought that only a small amount of relatively high energy electrons exist prior to the laser action. The electrons in turn collide with other bound electrons and release them in the avalanching process. In the case of metal, free electrons are available and instantly absorbing and redistributing energy. For any material, as the pulses get shorter laser induced breakdown (LIB) or ablation occurs only in the area where the laser intensity exceeds LIB or ablation threshold. There is essentially insufficient time for the surrounding area to react thermally. As pulses get shorter, vapor from the ablated material comes off after the deposition of the pulse, rather than during deposition, because the pulse duration is so short. In summary, by the method of the invention, laser induced breakdown of a material causes thermal-physical changes through ionization, free electron multiplication, dielectric breakdown, plasma formation, other thermal-physical changes in state, such as melting and vaporization, leading to an irreversible change in the material. It was also observed that the laser intensity also varies along the propagation axis (FIG. 13). The beam intensity as a function of R and Z expressed as:

$$I((Z, R)=I_o/(1+Z/Z_R)^2-\exp(-2R^2/W^2_z)$$

where $Z_R$ is the Rayleigh range and is equal to $$Z_R = \frac{\pi W_o^2}{\lambda}$$

$W_o$ is the beam size at the waist (Z=0).

We can see that the highest value of the field is at Z=R=0 at the center of the waist. If the threshold is precisely defined it is possible to damage the material precisely at the waist and have a damaged volume representing only a fraction of the waist in the R direction or in the Z direction. It is very important to control precisely the damage threshold or the laser intensity fluctuation.

For example, if the damage threshold or the laser fluctuations known within 10% that means that on the axis (R=0)

$$I(O,Z)/I_o=1(1=(Z/Z_R)^2=0.9$$

damaged volume can be produced at a distance $Z_R/3$ where $Z_R$ again is the Rayleigh range. For a beam waist of $W_o=\lambda$ then $$Z_R = \frac{\pi W_o^2}{\lambda} = \pi\lambda$$

and the d distance between hole can $$Z_R = \frac{\pi\lambda}{3}$$

as shown in FIG. 13.

The maximum intensity is exactly at the center of the beam waist (Z=0, R=0). For a sharp threshold it is possible to damage transparent, dielectric material in a small volume centered around the origin point (Z=0, R=0). The damage would be much smaller than the beam waist in the R direction. Small cavities, holes, or damage can have dimensions smaller than the Rayleigh range ($Z_R$) in the volume of the transparent, dielectric material. In another variation, the lens can be moved to increase the size of the hole or cavity in the Z direction. In this case, the focal point is essentially moved along the Z axis to increase the longitudinal dimension of the hole or cavity. These features are important to the applications described above and to related applications such as micro machining, integrated circuit manufacture, and encoding data in data storage media.

Advantageously, the invention identifies the regime where breakdown threshold fluence does not follow the scaling law and makes use of such regime to provide greater precision of laser induced breakdown, and to induce breakdown in a preselected pattern in a material or on a material. The invention makes it possible to operate the laser where the breakdown or ablation threshold becomes essentially accurate. The accuracy can be clearly seen by the I-bars along the curves of FIGS. 8 and 9. The I-bars consistently show lesser deviation and correspondingly greater accuracy in the regime at or below the predetermined pulse width.

While this invention has been described in terms of certain embodiment thereof, it is not intended that it be limited to the above description, but rather only to the extent set forth in the following claims.

The embodiments of the invention in which an exclusive property or privilege is claimed are defined in the appended claims.

We claim:

1. A method for laser induced breakdown (LIB) of a *non-biologic* material with a pulsed laser beam, the material being characterized by a relationship of fluence [breakdown] threshold *at which breakdown occurs* versus laser pulse width that exhibits a [rapid and] distinct change in slope at a characteristic laser pulse width, said method comprising the steps of:

a. generating [a beam of] *at least* one [or more] laser pulse[s in] which [each pulse] has a pulse width equal to or less than said characteristic laser pulse width; and b. [focusing said beam] *directing said pulse* to a point at or beneath the surface of the material.

2. The method according to claim 1 wherein the material is a metal, the pulse width is 10 to 10,000 femtoseconds, and the [beam] *pulse* has an energy of 1 nanojoule to 1 microjoule.

3. The method according to claim 1 wherein the spot size is varied within a range of 1 to 100 microns by changing the f number of the laser beam.

4. The method according to claim 1 wherein the spot size is varied within a range of 1 to 100 microns by varying the target position.

5. The method according to claim 1 wherein the material is transparent to radiation emitted by the laser and the pulse width is 10 to 10,000 femtoseconds, the [beam] *pulse* has an energy of 10 nanojoules to 1 millijoule.

[6. The method according to claim 1 wherein the material is biological tissue, the pulse width is 10 to 10,000 femtoseconds and the beam has an energy of 10 nanojoules to 1 millijoule.]

7. A method for laser induced breakdown (LIB) of a material with a pulsed laser beam, the material being characterized by a relationship of fluence breakdown threshold versus laser pulse width that exhibits a rapid and distinct change in slope at a predetermined laser pulse width where the onset of plasma induced breakdown occurs, said method comprising the steps of:

a. generating a beam of one or more laser pulses in which each pulse has a pulse width equal to or less than said predetermined laser pulse width obtained by determining the ablation (LIB) threshold of the material as a function of pulse width and by determining where the ablation (LIB) threshold function is no longer proportional to the square root of pulse width; and b. focusing said beam to a point at or beneath the surface of the material.

8. The method according to claim 1 wherein the laser [beam] *pulse* has an energy in a range of 10 nanojoules to 1 millijoule.

9. The method according to claim 1 wherein the laser [beam] *pulse* has a fluence in a range of 100 millijoules per square centimeter to 100 joules per square centimeter.

10. The method according to claim 1 wherein the laser [beam] *pulse* defines a spot in or on the material and the LIB causes ablation of an area having a size smaller than the area of the spot.

11. The method according to claim 1 wherein the laser [beam] *pulse* has a wavelength in a range of 200 nanometers to 2 microns.

12. The method according to claim 1 wherein the pulse width is in a range of a few picoseconds to femtoseconds.

13. The method according to claim 1 wherein the breakdown includes changes caused by one or more of ionization, free electron multiplication, dielectric breakdown, plasma formation, and vaporization.

14. The method according to claim 1 wherein the breakdown includes plasma formation.

15. The method according to claim 1 wherein the breakdown includes disintegration.

16. The method according to claim 1 wherein the breakdown includes ablation.

17. The method according to claim 1 wherein the breakdown includes vaporization.

18. The method according to claim 1 wherein the spot size is varied by flexible diaphragm to a range of 1 to 100 microns.

19. The method according to claim 1 wherein a mask is placed in the path of the beam to block a portion of the beam to cause the beam to assume a desired geometric configuration.

20. The method according to claim 1 wherein the laser operating mode is non-TEMoo.

21. The method according to claim 1 wherein the laser [beam] *pulse* defines a spot and has a lateral gaussian profile characterized in that fluence at or near the center of the [beam] *pulse* spot [it] *is* greater than the threshold fluence whereby the laser induced breakdown is ablation of an area within the spot.

22. The method according to claim [22] *21* wherein the spot size is a diffraction limited spot size providing an ablation cavity having a diameter less than the fundamental wavelength size.

23. The method according to claim 1 wherein the characteristic pulse width is obtained by determining the ablation (LIB) threshold of the material as a function of pulse width and determining where the ablation (LIB) threshold function is no longer proportional to the square root of pulse width.

24. A method for laser induced breakdown of a material which comprises:

a. generating a beam of one or more laser pulses in which each pulse has a pulse width equal to or less than a pulse width value corresponding to a change in slope of a curve of fluence breakdown threshold ($F_{th}$) as a function of laser pulse width (T), said change occurring at a point between first and second portions of said curve, said first portion spanning a range of relatively long pulse width where $F_{th}$ varies with the square root of pulse width ($T^{1/2}$) and said second portion spanning a range of short pulse width relative to said first portion with a $F_{th}$ versus T slope which differs from that of said first portion; and b. [focusing] *directing* said one or more pulses of said beam to a point at or beneath the surface of the material.

25. The method according to claim 24 and further including:

a. identifying a pulse width start point;

b. [focusing] *directing* the laser beam initial start point at or beneath the surface of the material; and c. scanning said beam along a predetermined path in a transverse direction.

26. The method according to claim 24 and further including:

a. identifying a pulse width start point;

b. [focusing] *directing* the laser beam initial start point at or beneath the surface of the material; and c. scanning said beam along a predetermined path in a longitudinal direction in the material to a depth smaller than the Rayleigh range.

27. The method according to claim 24 wherein the breakdown includes changes caused by one or more of ionization, free electron multiplication, dielectric breakdown, plasma formation, and vaporization.

28. The method according to claim 24 wherein the breakdown includes plasma formation.

29. The method according to claim 24 wherein the breakdown includes disintegration.

30. The method according to claim 24 wherein the breakdown includes ablation.

31. The method according to claim 24 wherein the breakdown includes vaporization.

32. The method according to any one of claims 1, 2, 5 or 24 wherein said beam is obtained by chirped-pulse amplification (CPA) means comprising means for generating a short optical pulse having a predetermined duration; means for stretching such optical pulse in time; means for amplifying such time-stretched optical pulse including solid state amplifying media; and means for recompressing such amplified pulse to its original duration.

33. A method for laser induced breakdown (LIB) of a *non-organic* material with a pulsed laser beam, the material being characterized by a relationship of fluence [breakdown] threshold *at which breakdown occurs* versus laser pulse width that exhibits a [rapid and] distinct change in slope at a predetermined laser pulse width where the onset of plasma induced breakdown occurs, said method comprising the steps of:

a. generating [a beam of] *at least* one [or more] laser pulse[s in] which [each pulse] has a pulse width equal to or less than said predetermined laser pulse width; and b. [focusing said beam] *directing said pulse* to a point at or beneath the surface of the material so that the laser beam defines a spot and has a lateral gaussian profile characterized in that fluence at or near the center of the beam spot is greater than the threshold fluence whereby the laser induced breakdown is ablation of an area within the spot.

34. The method according to claim 33 wherein the spot size is a diffraction limited spot size providing an ablation cavity having a diameter less than the fundamental wavelength size.

35. A method for laser induced breakdown (LIB) of a *non-biologic* material with a pulsed laser beam, the material being characterized by a relationship of fluence [breakdown] threshold *at which breakdown occurs* versus laser pulse width that exhibits a [rapid and] distinct change in slope at a predetermined laser pulse width where the onset of plasma induced breakdown occurs, said method comprising the steps of:

a. generating [a beam of] *at least* one [or more] laser pulse[s in] which [each pulse] has a pulse width equal to or less than said predetermined laser pulse width; and b. [focusing said beam] *directing said pulse* to a point at or beneath the surface of the material [which is biological tissue], the pulse width is 10 to 10,000 femtoseconds and the beam has an energy of 10 nanojoules to 1 millijoule.

36. A method for laser induced breakdown (LIB) of a material by plasma formation with a pulsed laser beam, the material being characterized by a relationship of fluence [breakdown] threshold *at which breakdown occurs* versus laser pulse width that exhibits a distinct change in slope at a characteristic laser pulse width, said method comprising the steps of:

a. generating [a beam of] *at least* one [or more] laser pulse[s in] which [each pulse] has a pulse width equal to or less than said characteristic laser pulse width, said characteristic pulse width being defined by the ablation (LIB) threshold of the material as a function of pulse width where the ablation (LIB) threshold function is no longer proportional to the square root of pulse width; and b. [focusing said beam] *directing said pulse* to a point at or beneath the surface of the material and inducing breakdown by plasma formation in the material.

37. A method for laser induced breakdown of a material which comprises:

a. determining, for a selected material, characteristic curve of fluence breakdown threshold ($F_{th}$) as a function of *the square root of* laser pulse width;

b. identifying a pulse width value on said curve corresponding to a [rapid and] distinct change in [slope of said $F_{th}$ versus pulse width curve] *the relationship between the fluence breakdown and the square root of pulse width* characteristic of said material;

c. generating a beam of one or more laser pulses, said *pulses* having a pulse width at or below said pulse width value corresponding to said distinct change in slope; and d. [focusing] *directing* said one or more pulses of said beam to a point at or beneath the surface of the material.

38. The method according to claim 37 and further including:

a. identifying a pulse width start point;

b. [focusing] *directing* the laser beam initial start point at or beneath the surface of the material; and c. scanning said beam along a predetermined path in a transverse direction.

39. The method according to claim 37 and further including:

a. identifying a pulse width start point;

b. [focusing] *directing* the laser beam initial start point at or beneath the surface of the material; and c. scanning said beam along a predetermined path in a longitudinal direction in the material to a depth smaller than the Rayleigh range.

40. The method according to claim 37 wherein the breakdown includes changes caused by one or more of ionization, free electron multiplication, dielectric breakdown, plasma formation, and vaporization.

41. The method according to claim 37 wherein the breakdown includes plasma formation.

42. The method according to claim 37 wherein the breakdown includes disintegration.

43. The method according to claim 37 wherein the breakdown includes ablation.

44. The method according to claim 37 wherein breakdown includes vaporization.

45. The method according to any one of claims 35, or 37 wherein said beam is obtained by chirped-pulse amplification (CPA) means comprising means for generating a short optical pulse having a predetermined duration; means for stretching such optical pulse in time; means for amplifying such time-stretched optical pulse including solid state amplifying media; and means for recompressing such amplified pulse to its original duration.

*46. A method for laser induced breakdown (LIB) of a metallic material with a pulsed laser beam, the material being characterized by a relationship of fluence threshold at which breakdown occurs versus laser pulse width that exhibits a distinct change in slope at a characteristic laser pulse width, said method comprising the steps of:*

*generating at least one laser pulse which has a pulse width equal to or less than said characteristic laser pulse width, said pulse having a width between 10 and 10,000 femtoseconds, and the pulse has an energy of 1 nanojoule to 1 microjoule; and*

*directing the pulse to a point at or beneath the surface of the material.*

*47. A method as in claim 46 wherein said beam is obtained by chirped pulse amplification (CPA) means comprising means for generating a short optical pulse having a predetermined duration;*

*means for stretching such optical pulse in time;*

*means for amplifying such stretched optical pulse including solid state amplifying media; and*

*means for recompressing such amplified pulse to its original duration.*

*48. A method for laser induced breakdown (LIB) of a metallic material transparent to radiation with a pulsed laser beam, the material being characterized by a relationship of fluence threshold at which breakdown occurs versus laser pulse width that exhibits a distinct change in slope at a characteristic laser pulse width, said method comprising the steps of:*

*generating at least one laser pulse which has a pulse width equal to or less than said characteristic laser pulse width, where the laser pulse width is 10 to 10,000 femtoseconds and the laser pulse has an energy of 10 nanojoules to 1 millijoule; and*

*directing the pulse to a point at or beneath the surface of the material.*

*49. A method as in claim 48 wherein said beam is obtained by chirped pulse amplification (CPA) means comprising means for generating a short optical pulse having a predetermined duration;*

*means for stretching such optical pulse in time;*

*means for amplifying such stretched optical pulse including solid state amplifying media; and*

*means for recompressing such amplified pulse to its original duration.*

*50. A method for laser induced breakdown (LIB) of a metallic material with a pulsed laser beam, the material being characterized by a relationship of fluence threshold at which breakdown occurs versus the square root of laser pulse width that exhibits a distinct change in slope at a characteristic laser pulse width;*

*determining the ablation (LIB) threshold of the material as a function of pulse width and determining where the ablation (LIB) threshold function is no longer proportional to the square root of pulse width;*

*generating at least one laser pulse which has a pulse width equal to or less than the characteristic pulse width; and*

*directing the pulse to a point at or beneath the surface of the material.*

*51. A method of optimally selecting a pulse width and fluence for a pulsed laser beam such that the pulsed laser induces laser induced breakdown (LIB) of a material, the material being characterized by a relationship of fluence threshold at which breakdown occurs versus the square root of laser pulse width comprising the step of identifying where the relationship between fluence threshold and the square root of pulse width exhibits a distinct change in slope and selecting the pulse width and fluence level associated with the distinct change in slope and directing the pulse at a point at or beneath the surface of the material.*

*52. The method as in claim 51 wherein the material is non-organic.*

*53. A method as in claim 51 wherein the material is organic.*

*54. A method for laser induced breakdown of a material with a pulsed laser beam, the material being characterized by a relationship of fluence threshold at which breakdown occurs versus the square root of laser pulse width that exhibits a distinct change in slope at a characteristic pulse width, said method comprising the steps of:*

*selecting a pulse width and fluence which is equal to or less than the distinct change in slope;*

*generating at least one laser pulse which has a pulse width equal to or less than the characteristic laser pulse width and fluence; and*

*directing said pulse to a point at or beneath the surface of a material.*

* * * * *

UNITED STATES PATENT AND TRADEMARK OFFICE

CERTIFICATE OF CORRECTION

PATENT NO. : RE 37,585 C1
APPLICATION NO. : 90/007102
DATED : March 6, 2007
INVENTOR(S) : Gérard Mourou et al.

It is certified that error appears in the above-identified patent and that said Letters Patent is hereby corrected as shown below:

Title Page, Item (10) Number: "US RE37,585 F1" should read --US RE37,585 C1--.

Signed and Sealed this

Seventh Day of October, 2008

JON W. DUDAS
*Director of the United States Patent and Trademark Office*

US00RE37585F1

(12) EX PARTE REEXAMINATION CERTIFICATE (5685th)

United States Patent

Mourou et al.

(10) Number: US RE37,585 F1

(45) Certificate Issued: Mar. 6, 2007

(54) METHOD FOR CONTROLLING CONFIGURATION OF LASER INDUCED BREAKDOWN AND ABLATION

(75) Inventors: Gérard Mourou, Ann Arbor, MI (US); Detao Du, Fremont, CA (US); Subrata K. Dutta, Ann Arbor, MI (US); Victor Elner, Ann Arbor, MI (US); Ron Kurtz, Ann Arbor, MI (US); Paul R. Lichter, Ann Arbor, MI (US); Xinbing Liu, Acton, MA (US); Peter P. Pronko, Dexter, MI (US); Jeffrey A. Squier, San Diego, CA (US)

(73) Assignee: Silicon Valley Bank, Santa Clara, CA (US)

Reexamination Request:
No. 90/007,102, Jun. 25, 2004

Reexamination Certificate for:

| | |
|---|---|
| Patent No.: | **Re. 37,585** |
| Issued: | **Mar. 19, 2002** |
| Appl. No.: | **09/366,685** |
| Filed: | **Aug. 4, 1999** |

Related U.S. Patent Documents

Reissue of:

| | |
|---|---|
| (64) Patent No.: | **5,656,186** |
| Issued: | **Aug. 12, 1997** |
| Appl. No.: | **08/224,961** |
| Filed: | **Apr. 8, 1994** |

(51) Int. Cl.
*B23K 26/02* (2006.01)
*B23K 26/40* (2006.01)

(52) U.S. Cl. ..... 219/121.69

(58) Field of Classification Search ..... None
See application file for complete search history.

(56) References Cited

U.S. PATENT DOCUMENTS

| | | | |
|---|---|---|---|
| 3,720,213 A | 3/1973 | Hobart et al. | |
| 4,001,840 A | 1/1977 | Becker et al. | |
| 4,087,672 A | 5/1978 | Yi | 219/121.68 |
| 4,114,018 A | 9/1978 | Von Allmen et al. | 219/121.69 |
| 4,289,378 A | 9/1981 | Remy et al. | |

(Continued)

FOREIGN PATENT DOCUMENTS

| | | |
|---|---|---|
| DE | 41 19024 | 12/1992 |
| EP | 0 842 729 A1 | 5/1998 |
| JP | 62-144893 | 6/1986 |
| JP | 62-093095 | 4/1987 |
| JP | 2-133185 | 5/1990 |
| JP | 403216287 A * | 9/1991 |
| JP | 5-63222 | 3/1993 |
| WO | WO 89/08529 | 3/1990 |

OTHER PUBLICATIONS

Mannion et al. "Ablation thresholds in ultrafast laser micro–machining of common metals in air" (2003), p. 476.*

(Continued)

*Primary Examiner*—Kiley Stoner

(57) ABSTRACT

In one aspect the invention provides a method for laser induced breakdown of a material with a pulsed laser beam where the material is characterized by a relationship of fluence breakdown threshold ($F_{th}$) versus laser beam pulse width (T) that exhibits an abrupt, rapid, and distinct change or at least a clearly detectable and distinct change in slope at a predetermined laser pulse width value. The method comprises generating a beam of laser pulses in which each pulse has a pulse width equal to or less than the predetermined laser pulse width value. The beam is focused to a point at or beneath the surface of a material where laser induced breakdown is desired.

The beam may be used in combination with a mask in the beam path. The beam or mask may be moved in the x, y, and Z directions to produce desired features. The technique can produce features smaller than the spot size and Rayleigh range due to enhanced damage threshold accuracy in the short pulse regime.

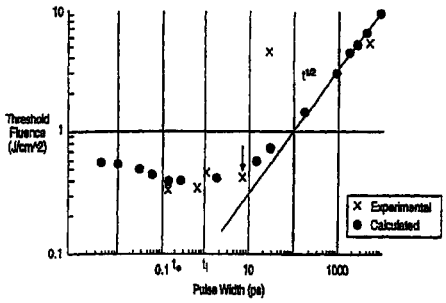

U.S. PATENT DOCUMENTS

| | | | | | |
|---|---|---|---|---|---|
| 4,464,761 | A | | 8/1984 | Alfano et al. | |
| 4,579,430 | A | | 4/1986 | Bille | |
| 4,630,274 | A | | 12/1986 | Schafer | |
| 4,665,913 | A | | 5/1987 | L'Esperance, Jr. | |
| 4,675,500 | A | | 6/1987 | Kunz et al. | 219/121.73 |
| 4,712,543 | A | | 12/1987 | Baron | |
| 4,727,381 | A | | 2/1988 | Bille et al. | |
| 4,729,372 | A | | 3/1988 | L'Esperance, Jr. | |
| 4,732,473 | A | | 3/1988 | Bille et al. | |
| 4,733,660 | A | | 3/1988 | Itzkan | |
| 4,764,930 | A | | 8/1988 | Bille et al. | |
| 4,838,679 | A | | 6/1989 | Bille | |
| 4,839,493 | A | | 6/1989 | Herziger et al. | 219/121.69 |
| 4,848,340 | A | | 7/1989 | Bille et al. | |
| 4,881,808 | A | | 11/1989 | Bille et al. | |
| 4,901,718 | A | | 2/1990 | Bille et al. | |
| 4,907,586 | A | | 3/1990 | Bille et al. | |
| 4,925,523 | A | | 5/1990 | Braren et al. | |
| 4,930,505 | A | | 6/1990 | Hatje | |
| 4,942,586 | A | | 7/1990 | Lai | |
| 4,988,348 | A | | 1/1991 | Bille | |
| 5,062,702 | A | | 11/1991 | Bille | |
| 5,093,548 | A | | 3/1992 | Schmidt-Hebbel | 219/121.71 |
| 5,098,426 | A | | 3/1992 | Sklar et al. | |
| 5,104,480 | A | | 4/1992 | Wojnarowski et al. | |
| 5,141,506 | A | | 8/1992 | York | |
| 5,207,668 | A | | 5/1993 | L'Esperance, Jr. | |
| 5,208,437 | A | | 5/1993 | Miyauchi et al. | 219/121.83 |
| 5,219,343 | A | | 6/1993 | L'Esperance, Jr. | |
| 5,235,606 | A | | 8/1993 | Mourou et al. | 372/25 |
| 5,243,589 | A | | 9/1993 | Stuke et al. | |
| 5,246,435 | A | | 9/1993 | Bille et al. | |
| 5,269,778 | A | | 12/1993 | Rink et al. | 606/12 |
| 5,280,491 | A | | 1/1994 | Lai | |
| 5,289,407 | A | | 2/1994 | Strickler et al. | |
| 5,312,396 | A | | 5/1994 | Feld et al. | |
| 5,335,258 | A | | 8/1994 | Whitlock | 378/122 |
| 5,348,018 | A | | 9/1994 | Alfano et al. | 606/10 |
| 5,389,786 | A | | 2/1995 | Itoh et al. | 250/307 |
| 5,454,902 | A | | 10/1995 | Zinck et al. | 219/121.69 |
| 5,461,212 | A | * | 10/1995 | Seiler et al. | 219/121.68 |
| 5,520,679 | A | | 5/1996 | Lin | |
| 5,558,789 | A | | 9/1996 | Singh | 219/121.69 |
| 5,575,936 | A | * | 11/1996 | Goldfarb | 219/121.68 |
| 5,606,588 | A | * | 2/1997 | Umstadter et al. | 378/119 |
| 5,637,244 | A | * | 6/1997 | Erokhin | 219/121.69 |
| 5,659,536 | A | | 8/1997 | Maillot et al. | |
| 5,741,245 | A | * | 4/1998 | Cozean et al. | 606/5 |
| 5,984,916 | A | | 11/1999 | Lai | |
| 6,322,556 | B1 | | 11/2001 | Gwon et al. | |
| 6,333,485 | B1 | | 12/2001 | Haight et al. | 219/121.68 |
| RE37,585 | E | | 3/2002 | Mourou et al. | |
| 6,489,589 | B1 | | 12/2002 | Alexander | |
| 2002/0125230 | A1 | | 9/2002 | Haight et al. | |

OTHER PUBLICATIONS

J. Phys.B: At. Mol. Opt. Phys. 32 (1999) R131–172, section 2.1.1.*

Kautek et al. (Appl. Phys. Lett. 69, 1996 p. 3146).*

Applied Physics A Materials Science & Processing, vol. 72, Issue 1, pp. 89–94 (2001), abstract.*

Schwab et al. (Appl. Phys. A 53, (1991) p. 282–283).*

Chen et al. Generation of submicron surface gratings of LiNbO3 by ultrashort UV laser pulses, 1997, 517–518.*

Baudach et al. "Femtosecond Laser Processing of Soft Materials", 29, 705(2001).*

N.K. Sherman, F. Brunel P.B. Corkum, F. Brunel, and F.A. Hegmann, Transient response of metals to ultrashort pulse excitation, 28 Optical Engineering No. 10 pp. 1114–1121 (1989).*

T. Beuermann, H.J. Brinkman, T. Damm and M. Stuke, Picosecond UV Excimer Laser Ablation of LiNbO3, Mat. Res. Soc. Symp. Proc., vol. 191 (1990).*

R. Srinivasan, E. Sutcliffe and B. Braren, Ablation and Etching of Polymethylmethacrylate by Very Short (160 fs) Ultraviolet (30 nm) Laser Pulses, Appl. Phys. Lett. 51 (16) pp. 1285–1287.*

C.V. Shank, R. Yen and C. Hirlimann, "Time Resolved Reflectivity Measures of Femtosecond–Optical–Pulse–Induced Phase transitions in Silicon", Physical Review Letters, vol. 50, No. 6, 454–457, Feb. 7, 1983.*

C.V. Shank, R. Yen, and C. Hirlimann, "Femtosecond–Time Resolved Surface Structural Dynamics of Optically Excited Silicon", Physical Review Letters, vol. 51, No. 10, 900–902, Sep. 5, 1983.*

C.V. Shank and M.C. Downer, "Femtosecond Dynamics of Highly Excited Semiconductors", Mat. Res. Soc. Symp. Proc., vol. 51, 15–23, 1985.*

S. Kuper and M. Stuke, "Femtosecond uv Excimer Laser Ablation", Applied Physics B, vol. 44, 199–201, Jun. 7, 1993.*

S. Preuss, M. Spath, Y. Zhang, and M. Stuke, "Time Resolved Dynamics of Subpicosecond Laser Ablation", Applied Physics Letters, vol. 62, No. 23, 3049–3051, Jun. 7, 1993.*

A.M. Malvezzi, N. Bloembergen, and C.Y. Huang, "Time–Resolved Picosecond Optical Measurements of Laser–Excited Graphite", Physical Review Letters, vol. 57, No. 1, 146–149, Jul. 7, 1986.*

D. H. Reitzke, X. Wang, H. Ahn, and M.C. Downer, "Femtosecond Laser Melting of Graphite", Physical Review B, vol. 40, No. 17, Dec. 15, 1989.*

F. Muller, K. Mann, R. Simon, J.S. Bernstein, and G.J. Zaal, "A comparative Study of Decomposition of Thin Films by Laser Induced PVD with Femtosecond and Nanosecond Laser Pulses", SPIE vol. 1858, pp. 464–475, 1993.*

International Search Report Form PCT/ISO/210 Dated Jul. 31, 1995 and Mailed Aug. 4, 1995.*

M.W. Berns et al., "Laser Microsurgery in Cell and Developmental Biology", Science, vol. 213, No. 31, pp. 505–513, Jul. 1981.*

G.L. LeCarpentier et al. "Continuous Wave Laser Ablation of Tissue: Analysis of Thermal and Mechanical Events", IEEE Transactions on Biomedical Engineering, vol. 40, No. 2, 188–200, Feb. 1993.*

C. LeBlanc, "Realization and Characterization of a High Intensity Femtosecond Laser System Based on all Titanium Doped Sapphire", Annales de Physique, vol. 19, No. 1, Abstract, Feb. 1994.*

R. Birngruber, C. Puliafito, A. Gawande, W. Lin, R. Schoenlein, and J. Fujimoto, "Femtosecond Laser–Tissue Interactions: Retinal Injury Studies", IEEE Journal of Quantum Electronics, vol. QE–23, No. 10, 1836–1844, Oct. 1987.*

B. Zysset, J. Fujimoto, and T. Deutsch, "Time–Resolved Measurements of Picosecond Optical Breakdown", Applied Physics B48, 139–147 (1989).*

B. Zysset, J. Fujimoto, C. Puliafito, R. Bingruber, and T. Deutsch, "Picosecond Optical Breakdown: Tissue Effects and Reduction of Collateral Damage", Lasers in Surgery and Medicine 9:192–204 (1989).*

S. Watanabe, R. Anderson, S. Brorson, G. Dalickas, J. Fujimoto, and T. Flotte, "Comparative Studies of Femtosecond to Microsecond Laser Pulses on Selective Pigmented Cell Injury in Skin", Photochemistry and Photobiology vol. 53, No. 6, 757–762, 1991.*
N. Bleombergen, "Laser–Induced Electric Breakdown in Solids", IEEE Journal of Quantum ELectronics, vol. QE–10, No. 3, (Mar. 1974).*
R. Birngruber, C. Puliafito, A. Gawandc, W. Lin, R. Schoenlein, and J. Fujimoto, Femtosecond Laser–Tissue Interactions: Retinal Injury Studies, IEEE Log. No. 8716039, (1987).*
D. Stern, R. Schoenlein, C. Puliafito, E. Dobi, R. Birngruber and J. Fujimoto, "Corneal Ablation by Nanosecond, Picosecond, and Femtosecond Lasers at 532 and 625 nm", Arch Opthalmol, vol. 107, (Apr. 1989).*
J. Squier, F. Salin, and G. Mourou, "100–fs Pulse Generation and Amplification in $TiAl_2 O_3$", Optics letters, vol. 16, No. 5 (Mar. 1991).*
B. Frueh, J. Bille, and S. Brown, "Intrastromal Relaxing Excisions in Rabbits with a Picosecond Infrared Laser", Lasers and Light in Opthamology, vol. 4, No. 3/4, pp. 165–168, (1992).*
R. Remmel, C. Dardennc, and J. Bille, "Intrasomal Tissue Removed Using an Infrared Picosecond Nd:YLF Opthalmic Laser Operating at 1053 nm", Lasers and Light in Opthamology, vol. 4, No. 3/4, 169–173, (1992).*
J. Squier and G. Mourou, "Tunable Solid State Lasers Create Ultrashort Pulses", Laser Focus World, (Jun. 1992).*
M.H. Niemz, T.P. Hoppeler, T. Juhasz, and J. Bille, "Intrastromal Ablations for Refractive Corneal Surgery Using Picosecond Infrared Laser Pulses", Lasers and Light in Opthamology, vol. 5, No. 3, pp. 149–155, 1993.*
H. Cooper, J. Schuman, C. Puliafito, D. McCarthy, W. Woods, N. Friedmann, N. Wang, and C. Lin, "Picosecond Neodymium:Yttrium Lithium Fluoride Laser Sclerectomy", Am. Journal of Opth. 115:221–224, (Feb. 1993).*
K. Frederickson, W. White, R. Wheeland, and D. Slaughter, "Precise Ablation of Skin with Reduced Collateral Damage Using the Femtosecond–Pulsed, Terawatt Titanium–Sapphire Laser", Arch Dermatol, vol. 129, (Aug. 1993).*
H. Kapteyn and M. Murnane, "Femtosecond Lasers: The next Generation", Optics & Photonics News, (Mar. 1994).*
G. Mourou, A. Zewail, P. Barbara, and W. Knox, "New Generation of Ultrafast Sources Marked by Higher Powers, Versatility" Optics & Photonics News (Mar. 1994).*
D. Du, X. Lin, G. Korn, J. Squier, and G. Morou, "Laser–Induced Breakdown by Impact Ionization in $SiO_2$ with Pulsse Widths from 7 ns to 150 fs", Appl. Phys. letters 64(23), (Jun. 6, 1994).
Bauermann, Th., et al., "Picosecond UV Excimer Laser Ablation of LiNbO3," published 1990, Materials Research Society, vol. 191, pp. 37–42.
Sherman, N.K., et al., "Transient response of metals to ultrashort pulse excitation," Oct. 1989, Optical Engineering, vol. 28 No. 10, pp. 1114–1121.
Srinivasan, R., Sutcliffe, et al., "Ablation and etching of polymethylmethacrylate by very short (160 fs) ultraviolet (308 nm) laser pulses", accepted for publication Aug. 24, 1987, American Institute of Physics, pp. 1285–1287.
"Femtosecond–Pulse Laser Ablation of Human Corneas", W. Kautek et al. Applied Physics A 58 213–518 (1994).
"Nanosecond and Femtosecond Excimer Ablation of Fused Silica" by Ihlemann et al., Applied Physics A. 54, pp. 363–368. Dec. 1992.
Wolfgang Kautek and Jorg Kruger "Femtosecond Pulse Laser Ablation of Metallic, Semiconducting, Ceramic and Biological Materials," SPIE, vol. 2207, pp. 600–607, 611. Apr. 1994.
Corkum et al., "Thermal Response of Metals to Ultrashort–Pulse Laser Excitation", Phys. Rev. Lett. vol. 61, No. 25, pp. 2886–2889 (Dec. 19, 1988).
Soileau et al., "Temporal Dependence of Laser–Induced Breakdown in NaCL and SiO2", Lser Induced Damage in Optical Materials, 1982 Proceedings of a Symposium (NBS–SP–669). NBS, Boulder CO, USA, 1984; IX+488, pp. 387–405.
Kuper et al., "Ablation of UV–Transparent Materials with Femtosecond UV Excimer Laser Pulses", Microelectronic Engineering 9, pp. 475–480 (1989).

* cited by examiner

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 6 and 11 are cancelled.

Claims 1, 3, 4, 7, 24, 33, 35, 36, 37, 42–44, 46, 48 and 50–54 are determined to be patentable as amended.

Claims 2, 5, 8–10, 12–23, 25–32, 34, 38–41, 45, 47 and 49, dependent on an amended claim, are determined to be patentable.

New claims 55–64 are added and determined to be patentable.

1. A method for laser induced breakdown (LIB) of a non-biologic material with a pulsed laser beam, the material being characterized by a relationship of fluence threshold at which breakdown occurs versus laser pulse width that exhibits a distinct change in slope at a characteristic laser pulse width, said method comprising the steps of:

a. generating [at least one] *a* laser pulse which has a pulse width equal to or less than said characteristic laser pulse width *at a fluence to cause a breakdown effect by itself at a wavelength of 800 nanometers to 2 microns*; and b. directing said pulse to a point at or beneath the surface of the material.

3. The method according to claim 1 wherein [the] *a* spot size is varied within a range of 1 to 100 microns by changing the f number of the laser beam.

4. The method according to claim 1 wherein [the] *a* spot size is varied within a range of 1 to 100 microns by varying the target position.

7. A method for laser induced breakdown (LIB) of a material *being at least one member selected from the group consisting of biologic materials and transparent materials* with a pulsed laser beam, the material being characterized by a relationship of fluence breakdown threshold versus laser pulse width that exhibits a rapid and distinct change in slope at a predetermined laser pulse width where the onset of plasma induced breakdown occurs, said method comprising the steps of:

a. generating a beam of one or more laser pulses in which each pulse has a pulse width equal to or less than said predetermined laser pulse width obtained by determining the ablation *fluence* (LIB) threshold of the material as a function of pulse width and by determining where the ablation (LIB) *fluence* threshold function is no longer proportional to the square root of pulse width *and in which each pulse has a fluence greater than 5 joules per square centimeter to cause an ablation breakdown effect by itself*; and b. focusing said beam to a point at or beneath the surface of the material.

24. A method for laser induced breakdown of a material *being at least one member selected from the group consisting of biologic materials and transparent materials* which comprises:

a. generating a beam of one or more laser pulses in which each pulse has a pulse width equal to or less than a pulse width value corresponding to a change in slope of a curve of fluence breakdown threshold ($F_{th}$) as a function of laser pulse width (T), said change occurring at a point between first and second portions of said curve, said first portion spanning a range of relatively long pulse width where $F_{th}$ varies with the square root of pulse width ($T^{1/2}$) and said second portion spanning a range of short pulse width relative to said first portion with a $F_{th}$ versus T slope which differs from that of said first portion, *provided that at least one of the following two conditions applies: (i) each pulse has a fluence greater than predicted for a pulse by the slope of the first curve portion, to cause breakdown by itself; and (ii) each pulse has a fluence greater than predicted for a pulse by the second curve portion*; and b. directing said one or more pulses of said beam to a point at or beneath the surface of the material.

33. A method for laser induced breakdown (LIB) of a non-organic material with a pulsed laser beam, the material being characterized by a relationship of fluence threshold at which breakdown occurs versus laser pulse width that exhibits a distinct change in slope at a predetermined laser pulse width where the onset of plasma induced breakdown occurs, said method comprising the steps of:

a. generating [at least one] *a* laser pulse which has a pulse width equal to or less than said predetermined laser pulse width *at a fluence to cause ablation by itself*; and b. directing said pulse to a point at or beneath the surface of the material so that the laser beam defines a spot and has a lateral gaussian profile characterized in that fluence at or near the center of the beam spot is greater than the threshold fluence whereby the laser induced breakdown is ablation of an area within the spot.

35. A method for laser induced breakdown (LIB) of a non-biologic material with a pulsed laser beam, the material being characterized by a relationship of fluence threshold at which breakdown occurs versus laser pulse width that exhibits a distinct change in slope at a predetermined laser pulse width where the onset of plasma induced breakdown occurs, said method comprising the steps of:

a. generating [at least one] *a* laser pulse which has a pulse width equal to or less than said predetermined laser pulse width; and b. directing said pulse to a point at or beneath the surface of the material, the pulse width is 10 to 10,000 femtoseconds and the beam has an energy of 10 nanojoules to 1 millijoule *and the pulse has a fluence to cause breakdown by itself*.

36. A method for laser induced breakdown (LIB) of a material by plasma formation with a pulsed laser beam, the material being characterized by a relationship of fluence threshold at which breakdown occurs versus laser pulse width that exhibits a distinct change in slope at a characteristic laser pulse width *defining a first curve portion of relatively long pulse width and a second curve portion of relatively short pulse width*, said method comprising the steps of:

a. generating [at least one laser pulse which has] *one or more laser pulses which have* a pulse width equal to or less than said characteristic laser pulse width, said characteristic pulse width being defined by the ablation (LIB) *fluence* threshold of the material as a function of pulse width where the ablation (LIB) *fluence* threshold function is no longer proportional to the square root of pulse width; *provided that at least one of the following two conditions applies: (i) each pulse has a fluence greater than predicted for a pulse by the slope of the first curve portion, to cause ablation by itself; and (ii) each pulse has a fluence greater than predicted for a pulse by the second curve portion*; and b. directing said pulse to a point at or beneath the surface of the material and inducing breakdown by plasma formation in the material.

37. A method for laser induced breakdown of a *selected* material which comprises:

a. determining, for [a] *the* selected material, characteristic curve of fluence breakdown threshold ($F_{th}$) as a function of the square root of laser pulse width;

b. identifying a pulse width value on said curve corresponding to a distinct change in the relationship between the fluence breakdown and the square root of pulse width characteristic of said material;

c. generating a [beam of one or more laser pulses, said pulses] *beam having a laser pulse* having a pulse width at or below said pulse width value corresponding to said distinct change in slope *and at a fluence to cause breakdown by itself*; and d. directing said [one or more pulses of said beam] *pulse* to a point at or beneath the surface of the material.

42. [The method according to claim 37] *A method for laser induced breakdown of a selected material which comprises:*

*a. determining, for the selected material, characteristic curve of fluence breakdown threshold ($F_{th}$) as a function of the square root of laser pulse width;*

*b. identifying a pulse width value on said curve corresponding to a distinct change in the relationship between the fluence breakdown and the square root of pulse width characteristic of said material;*

*c. generating a beam of one or more laser pulses, each of said pulses having a pulse width at or below said pulse with value corresponding to said distinct change in slope and at a fluence to cause breakdown by itself; and*

*d. directing said one or more pulses of said beam to a point at or beneath the surface of the material;* wherein the breakdown includes disintegration.

43. [The method according to claim 37] *A method for laser induced breakdown of a selected material which comprises:*

*a. determining, for the selected material, characteristic curve of fluence breakdown threshold ($F_{th}$) as a function of the square root of laser pulse width;*

*b. identifying a pulse width value on said curve corresponding to a distinct change in the relationship between the fluence breakdown and the square root of pulse width characteristic of said material;*

*c. generating a beam of one or more laser pulses, each of said pulses having a pulse width at or below said pulse width value corresponding to said distinct change in slope and at a fluence to cause breakdown by itself; and*

*d. directing said one or more pulses of said beam to a point at or beneath the surface of the material;* wherein the breakdown includes ablation.

44. [The method according to claim 37] *A method for laser induced breakdown of a selected material which comprises:*

*a. determining, for the selected material, characteristic curve of fluence breakdown threshold ($F_{th}$) as a function of the square root of laser pulse width;*

*b. identifying a pulse width value on said curve corresponding to a distinct change in the relationship between the fluence breakdown and the square root of pulse width characteristic of said material;*

*c. generating a beam of one or more laser pulses, each of said pulses having a pulse width at or below said pulse width value corresponding to said distinct change in slope and at a fluence to cause breakdown by itself; and*

*d. directing said one or more pulses of said beam to a point at or beneath the surface of the material;* wherein *the* breakdown includes vaporization.

46. A method for laser induced breakdown (LIB) of a metallic material with a pulsed laser beam, the material being characterized by a relationship of fluence threshold at which breakdown occurs versus laser pulse width that exhibits a distinct change in slope at a characteristic laser pulse width, said method comprising the steps of:

generating [at least one] *a* laser pulse which has a pulse width equal to or less than said characteristic laser pulse width, said pulse having a width between 10 and 10,000 femtoseconds, and the pulse has an energy of 1 nanojoule to 1 microjoule*, and the pulse has a fluence to cause breakdown by itself;* and directing the pulse to a point at or beneath the surface of the material.

48. A method for laser induced breakdown (LIB) of a [metallic] material transparent to radiation with a pulsed laser beam, the material being characterized by a relationship of fluence threshold at which breakdown occurs versus laser pulse width that exhibits a distinct change in slope at a characteristic laser pulse width, said method comprising the steps of:

generating [at least one] *a* laser pulse which has a pulse width equal to or less than said characteristic laser pulse width, where the laser pulse width is 10 to 10,000 femtoseconds and the laser pulse has an energy of 10 nanojoules to 1 millijoule, *and the pulse has a fluence greater than 5 joules per square centimeter to cause breakdown by itself*; and directing the pulse to a point at or beneath the surface of the material.

50. A method for laser induced breakdown (LIB) of a [metallic] *metal* material with a pulsed laser beam, the material being characterized by a relationship of fluence threshold at which breakdown occurs versus the square root of laser pulse width that exhibits a distinct change in slope at a characteristic laser pulse width;

determining the ablation (LIB) threshold of the material as a function of pulse width and determining where the ablation (LIB) threshold function is no longer proportional to the square root of pulse width;

generating [at least one] *a* laser pulse which has a pulse width equal to or less than the characteristic pulse width *at a fluence to cause ablation by itself*; and directing the pulse to a point at or beneath the surface of the material.

51. A method of optimally selecting a pulse width and fluence for a pulsed laser beam such that the pulsed laser induces laser induced breakdown (LIB) of a material *being at least one member selected from the group consisting of biologic materials and transparent materials*, the material being characterized by a relationship *curve* of fluence threshold at which breakdown occurs versus the square root of laser pulse width comprising the step of identifying where the relationship between fluence threshold and the square root of pulse width exhibits a distinct change in slope *defining a first curve portion of relatively long pulse width and a second curve portion of relatively short pulse width* and selecting the pulse width [and fluence level] associated with the distinct change in slope *and selecting a fluence level according to at least one of the following two conditions: (i) the fluence is greater than predicted for a pulse by the slope of the first curve portion, to cause ablation by itself; and (ii) the fluence is greater than predicted for a pulse by the second curve portion;* and directing the pulse at a point at or beneath the surface of the material.

52. [The method as in claim 51 wherein the material is non-organic] *A method of optimally selecting a pulse width and fluence for a pulsed laser beam such that the pulsed laser induces laser induced breakdown (LIB) of a non-organic material, the material being characterized by a relationship of fluence threshold at which breakdown occurs versus the square root of laser pulse width comprising the step of identifying where the relationship between fluence threshold and the square root of pulse width exhibits a distinct change in slope and selecting the pulse width associated with the distinct change in slope and a fluence level for a pulse by itself to cause breakdown and the wavelength is 800 nanometers to 2 microns, and directing the pulse at a point at or beneath the surface of the material.*

53. [A method as in claim 51 wherein the material is organic] *A method of optimally selecting a pulse width and fluence for a pulsed laser beam such that the pulsed laser induces laser induced breakdown (LIB) of a material being at least one member selected from the group consisting of biologic materials and transparent materials, the material being characterized by a relationship of fluence threshold at which breakdown occurs versus the square root of laser pulse width comprising the step of identifying where the relationship between fluence threshold and the square root of pulse width exhibits a distinct change in slope and a fluence level greater than 5 joules per square centimeter for a pulse by itself to cause breakdown; and directing the pulse at a point at or beneath the surface of the material.*

54. A method for laser induced breakdown of a material with a pulsed laser beam, the material being characterized by a relationship of fluence threshold at which breakdown occurs versus the square root of laser pulse width that exhibits a distinct change in slope at a characteristic pulse width, said method comprising the steps of:

selecting a pulse width [and fluence] which is equal to or less than the distinct change in slope;

generating [at least one] *a* laser pulse which has a pulse width equal to or less than the characteristic laser pulse width [and] *at a* fluence *to cause a breakdown effect by itself, provided that when said material is biologic said fluence is greater than 5 joules per square centimeter, and when said material is non-biologic said wavelength is 800 nanometers to 2 microns*; and directing said pulse to as point at or beneath the surface of a material.

*55. A method for laser induced breakdown (LIB) of a material being at least one member selected from the group consisting of biologic materials and transparent materials with a pulsed laser beam, the material being characterized by a relationship of fluence threshold at which breakdown occurs versus laser pulse width that exhibits a distinct change in slope at a characteristic laser pulse width, said method comprising the steps of:*

*a. generating laser pulses, each of which has a pulse width equal to or less than said characteristic laser pulse width at a fluence greater than 5 joules per square centimeter by itself to cause a breakdown effect at respective coordinates;*

*b. directing said pulses to the material;*

*characterized in that said breakdown effect is ablation reproduced at each of the respective coordinates by a respective one of said laser pulses.*

*56. A method for laser induced breakdown (LIB) of a material with a pulsed laser beam, the material being characterized by a relationship of fluence threshold at which breakdown occurs versus laser pulse width that exhibits a distinct change in slope at a characteristic laser pulse width, said method comprising:*

*a. generating a laser pulse which has a pulse width equal to or less than said characteristic laser pulse width at a fluence to cause a breakdown effect with a single laser pulse, provided that when said material is biologic said fluence is greater than 5 joules per square centimeter, and when said material is non-biologic said wavelength is 800 nanometers to 2 microns; and*

*b. directing said pulse to a point at or beneath the surface of the material.*

*57. The method of claim 56 wherein a plurality of pulses are generated each of which causes a breakdown effect.*

*58. The method of claim 57 wherein a respective one of said plurality of said pulses is directed at a respective coordinate.*

*59. A method for laser induced breakdown (LIB) of a material being at least one member selected from the group consisting of biologic materials and transparent materials with a pulsed laser beam, the material being characterized by a relationship of fluence threshold at which breakdown occurs versus the square root of laser pulse width that exhibits a distinct change in slope at a characteristic pulse width, said method comprising:*

*selecting a pulse width which is equal to or less than the distinct change in slope and selecting a fluence greater than 5 joules per square centimeter to cause a breakdown effect with a single laser pulse;*

*generating a laser pulse which has the selected pulse width and the selected fluence; and*

*directing said pulse to a point at or beneath the surface of a material;*

*characterized in that said breakdown effect is reproducible at respective coordinates by a respective said laser pulse having the selected pulse width and fluence.*

*60. The method of claim 59 wherein a plurality of pulses are generated each of which causes a breakdown effect.*

*61. The method of claim 60 wherein a respective one of said plurality of said pulses is directed at a respective one of said respective coordinates.*

*62. A method for laser induced breakdown (LIB) of a material with a pulsed laser beam, the material being characterized by a relationship of fluence threshold at which breakdown occurs versus laser pulse width that exhibits a distinct change in slope at a characteristic laser pulse width defining a first curve portion of relatively long pulse width and a second curve portion of relatively short pulse width, said method comprising:*

*a. generating a laser pulse which has a pulse width equal to or less than said characteristic laser pulse width at a fluence according to at least one of the following conditions: (i) the fluence is greater than predicted for a pulse by the slope of the first curve portion, to cause*

*ablation by itself; and (ii) the fluence is greater than predicted for a pulse by the second curve portion; and*

*b. directing said pulse to a point at or beneath the surface of the material;*

*characterized in that said breakdown effect is reproducible at respective coordinates by a respective said laser pulse.*

*63. The method of claim 62 wherein a plurality of pulses are generated each of which causes a breakdown effect.*

*64. The method of claim 63 wherein a respective one of said plurality of said pulses is directed at a respective one of said respective coordinates.*

* * * * *